(12) United States Patent  
Berezin et al.

(10) Patent No.: US 12,174,104 B2  
(45) Date of Patent: Dec. 24, 2024

(54) SYNTHESIS, POST-MODIFICATION AND SEPARATION OF BIOLOGICS USING ACOUSTICALLY CONFINED SUBSTRATES

(71) Applicants: Mikhail Y. Berezin, St. Louis, MO (US); John Mark Meacham, St. Louis, MO (US); Michael Binkley, St. Louis, MO (US)

(72) Inventors: Mikhail Y. Berezin, St. Louis, MO (US); John Mark Meacham, St. Louis, MO (US); Michael Binkley, St. Louis, MO (US)

(73) Assignee: Washington University, St. Louis, MO (US)

( * ) Notice: Subject to any disclaimer, the term of this patent is extended or adjusted under 35 U.S.C. 154(b) by 934 days.

(21) Appl. No.: 17/222,358

(22) Filed: Apr. 5, 2021

(65) Prior Publication Data

US 2021/0239591 A1  Aug. 5, 2021

Related U.S. Application Data

(63) Continuation of application No. 15/998,836, filed on Aug. 16, 2018, now Pat. No. 10,969,324.

(Continued)

(51) Int. Cl.
```
G01N 15/1404    (2024.01)
B01L 3/00       (2006.01)
G01N 33/543     (2006.01)
```

(52) U.S. Cl.  
CPC .... *G01N 15/1404* (2013.01); *B01L 3/502753* (2013.01); *B01L 3/502761* (2013.01);  
(Continued)

(58) Field of Classification Search  
None  
See application file for complete search history.

(56) References Cited

U.S. PATENT DOCUMENTS 10,807,029 B2  10/2020  Meacham et al.  
2001/0036674 A1  11/2001  Indermuhle et al.  
(Continued)

FOREIGN PATENT DOCUMENTS

RU  2480522 C2  4/2013  
WO  2008107652 A1  9/2008

OTHER PUBLICATIONS

Li Peng et al., "Acoustic separation of circulating tumor cells," PNAS, 112(16): 4970-4975 (Apr. 21, 2015).

*Primary Examiner* — Matthew D Krcha  
*Assistant Examiner* — Brittany I Fisher  
(74) *Attorney, Agent, or Firm* — Armstrong Teasdale LLP

(57) ABSTRACT

Disclosed herein is are methods for isolating mammalian cells under continuous flow conditions, enriching mammalian cells under continuous flow conditions, and enriching microorganisms under continuous flow conditions. The methods include providing and loading a plurality of mammalian cells or microorganisms into an acoustic separation device. The acoustic separation device includes: an inlet; an outlet; a channel coupled to the inlet and the outlet, wherein the channel defines a flow path between the inlet and the outlet; a standing acoustic wave generating device; and at least one pillar array comprising a plurality of pillars, wherein the at least one pillar array is situated within the flow path defined by the channel, wherein the at least one pillar array includes a first pillar array and a second pillar array, wherein the first pillar array is substantially parallel to the second pillar array, wherein the first pillar array and the second pillar array form an enrichment structure. The methods further include generating an augmented pressure field (Continued)

comprising locally augmenting, by the enrichment structure, a pressure field generated by the standing acoustic wave generating device.

20 Claims, 29 Drawing Sheets
(18 of 29 Drawing Sheet(s) Filed in Color)

Related U.S. Application Data

(60) Provisional application No. 62/546,261, filed on Aug. 16, 2017.

(52) U.S. Cl.
CPC ............... *G01N 33/54373* (2013.01); *B01L 2200/0636* (2013.01); *B01L 2200/0652* (2013.01); *B01L 2300/0829* (2013.01); *B01L 2300/0864* (2013.01); *B01L 2400/0436* (2013.01); *B01L 2400/086* (2013.01); *G01N 2015/142* (2013.01)

(56) References Cited

U.S. PATENT DOCUMENTS

| | | |
|---|---|---|
| 2003/0102263 A1 | 6/2003 | Lopez et al. |
| 2005/0211556 A1* | 9/2005 | Childers ............... B03C 5/028 204/627 |
| 2006/0070951 A1 | 4/2006 | Baba et al. |
| 2006/0266692 A1 | 11/2006 | Foster et al. |
| 2010/0066346 A1 | 3/2010 | Zhang et al. |
| 2013/0213488 A1 | 8/2013 | Weitz et al. |
| 2014/0008307 A1 | 1/2014 | Guldiken et al. |
| 2014/0256031 A1 | 9/2014 | Kobayashi et al. |
| 2014/0273229 A1 | 9/2014 | Meacham et al. |
| 2015/0219623 A1 | 8/2015 | Doria et al. |
| 2015/0321129 A1 | 11/2015 | Lipkens et al. |
| 2016/0008532 A1 | 1/2016 | Fiering et al. |
| 2016/0123857 A1 | 5/2016 | Kapur et al. |
| 2019/0076769 A1 | 3/2019 | Meacham et al. |

* cited by examiner

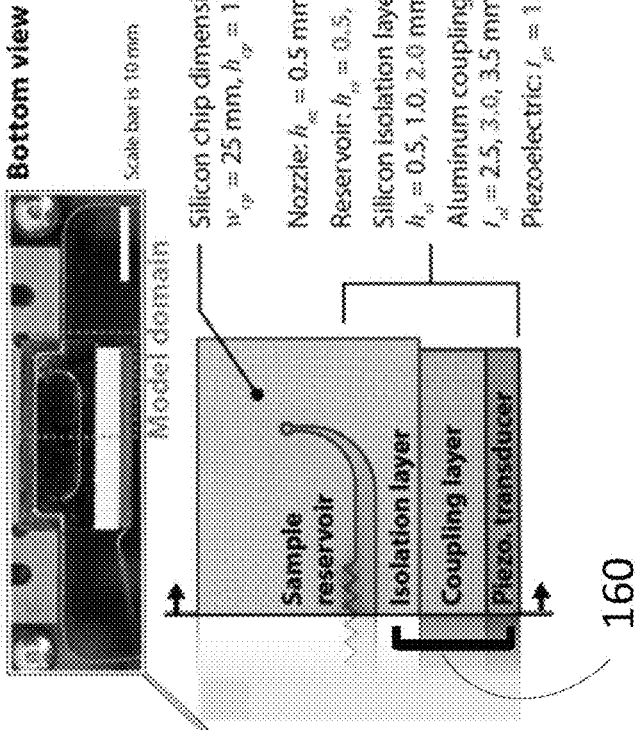
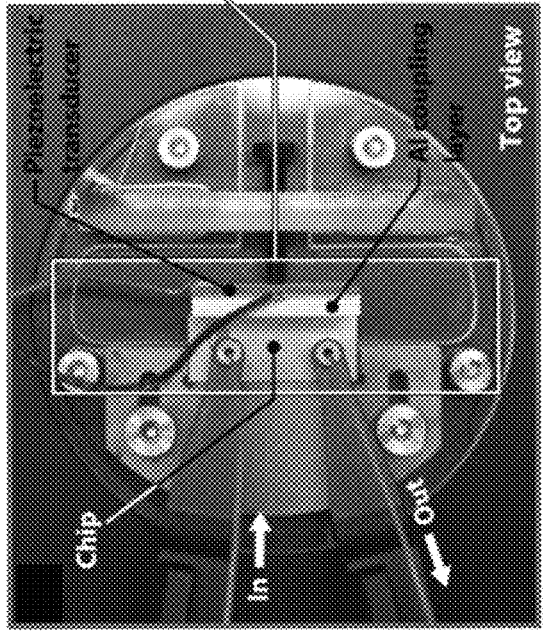
FIG. 6A  FIG. 6B  FIG. 6C

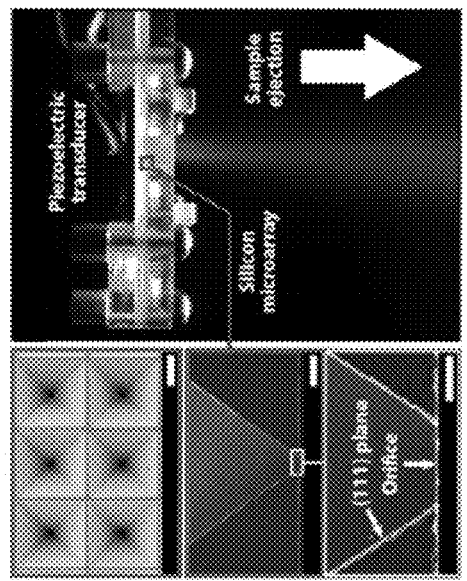
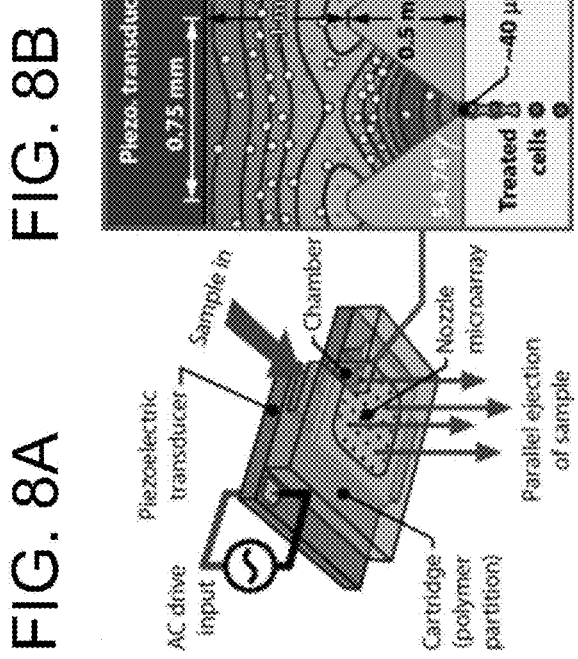
FIG. 8A  FIG. 8B
FIG. 8C
FIG. 8D
FIG. 8E
FIG. 8F

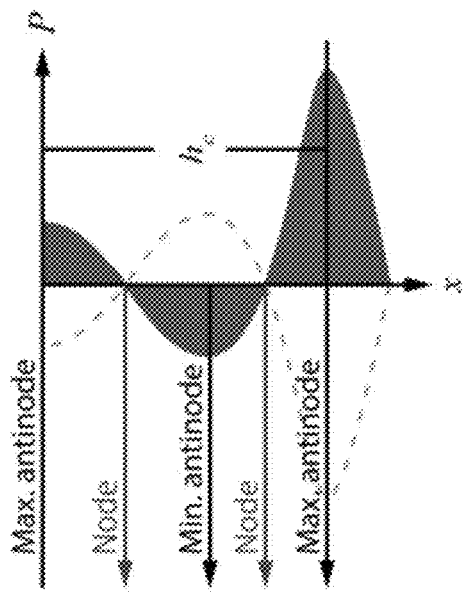
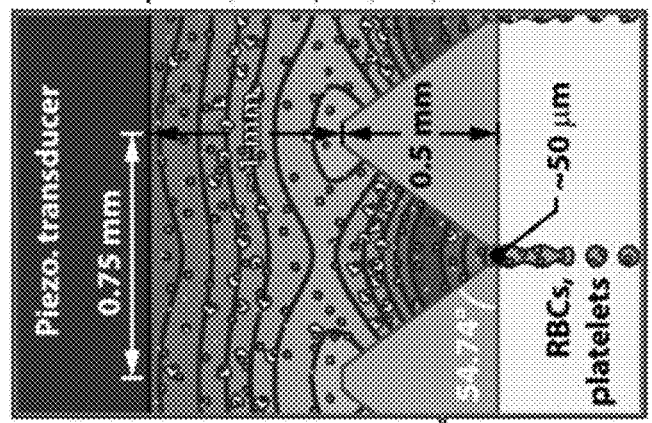
FIG. 10A
FIG. 10B
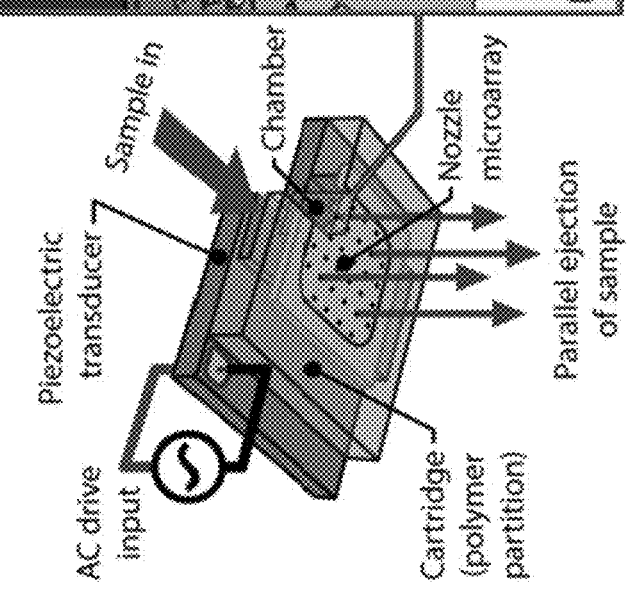

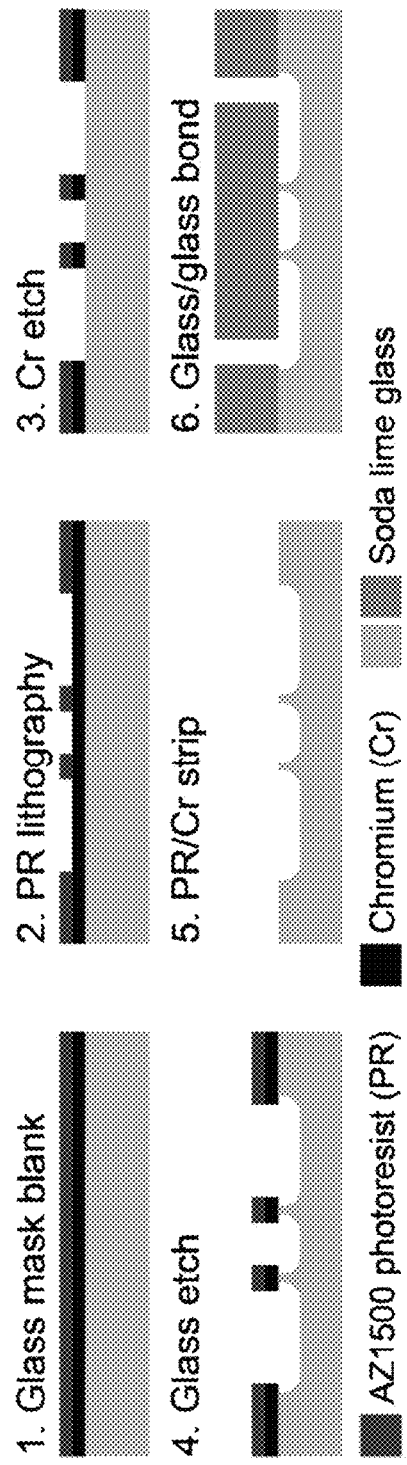
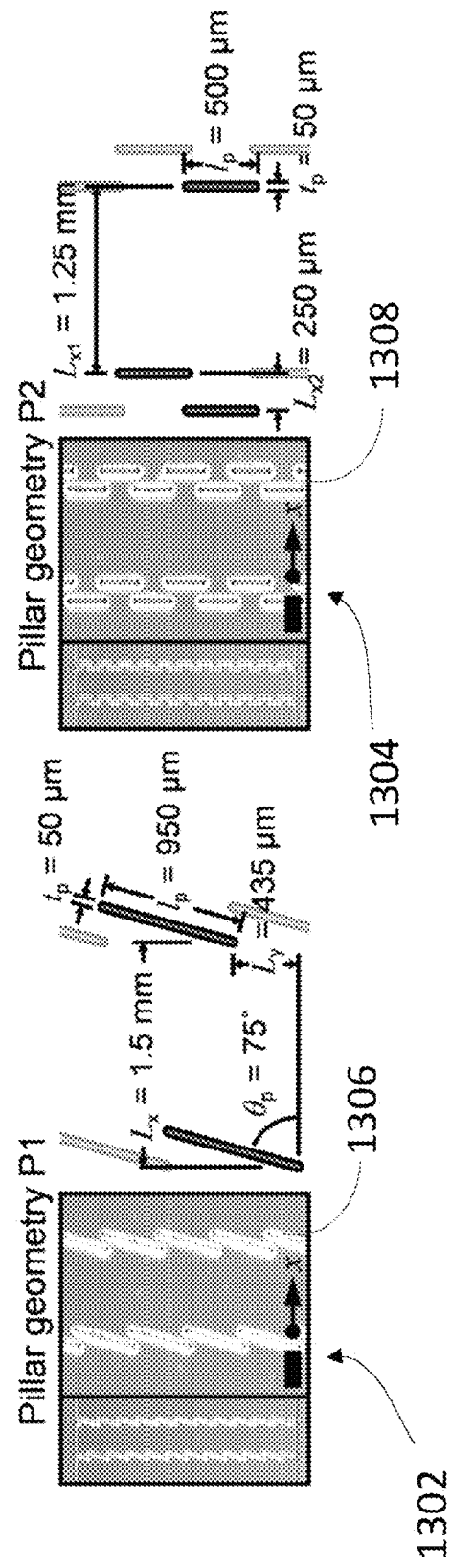
FIG. 13A
FIG. 13B
FIG. 13C

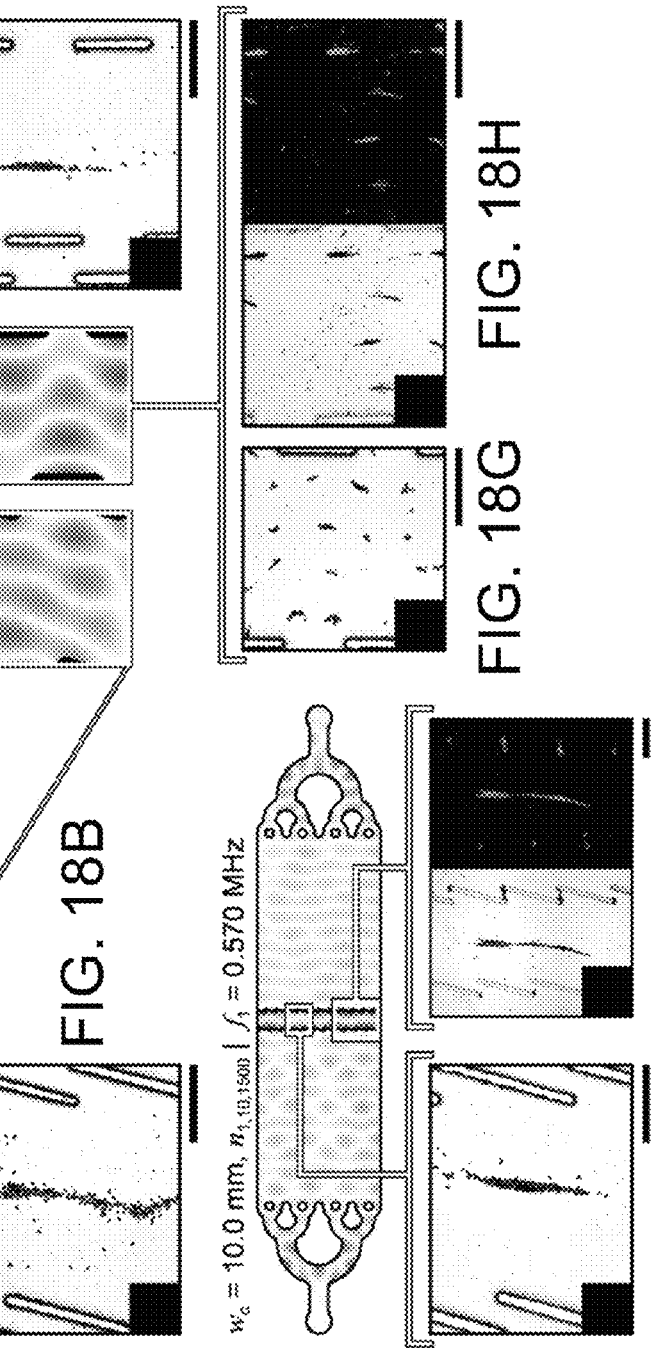
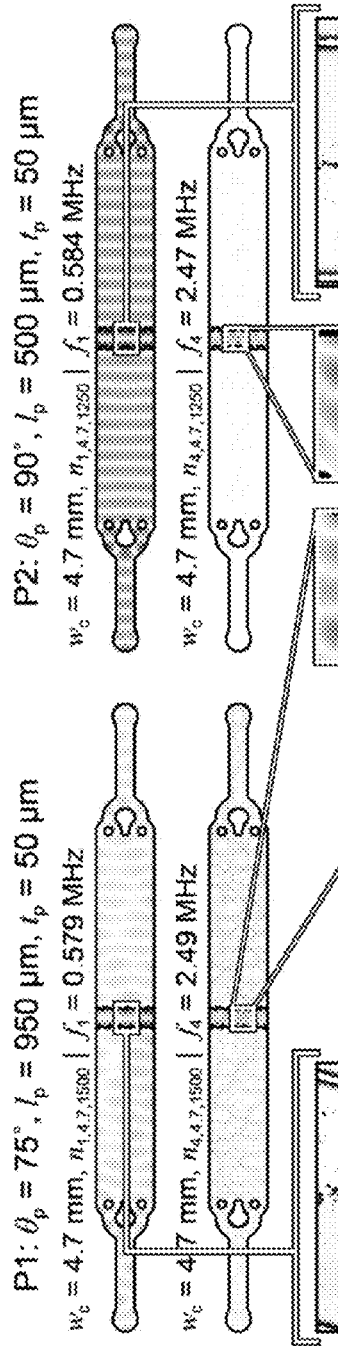
FIG. 18A  FIG. 18E
FIG. 18B  FIG. 18F
FIG. 18C  FIG. 18G
FIG. 18D  FIG. 18H

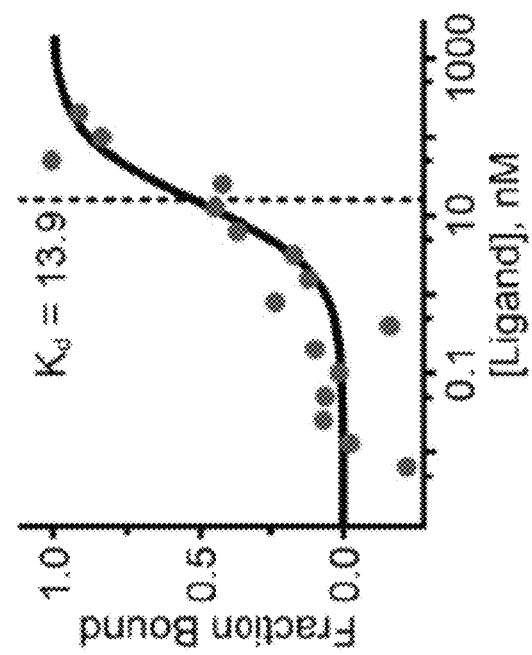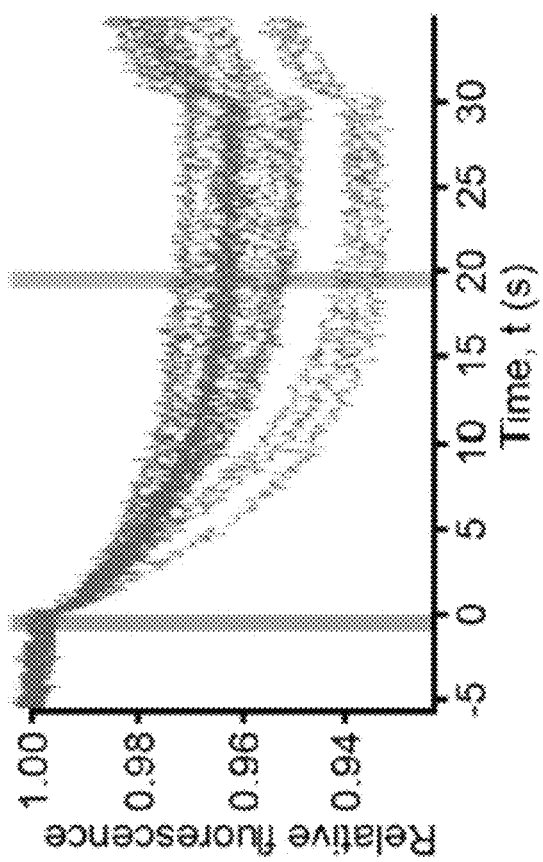
FIG. 29A
FIG. 29B

SYNTHESIS, POST-MODIFICATION AND SEPARATION OF BIOLOGICS USING ACOUSTICALLY CONFINED SUBSTRATES

CROSS-REFERENCE TO RELATED APPLICATIONS

This application is a continuation of U.S. patent application Ser. No. 15/998,836 filed Aug. 16, 2018, now U.S. Pat. No. 10,969,324 issued Apr. 6, 2021, which claims priority from U.S. Provisional Application No. 62/546,261 filed Aug. 16, 2017. These applications are incorporated herein in their entireties.

STATEMENT REGARDING FEDERALLY SPONSORED RESEARCH & DEVELOPMENT

This invention was made with government support under grant NCI/NIH CA198419, awarded by the National Cancer Institute of the U.S. National Institutes of Health. The government has certain rights in the invention.

BACKGROUND

Automation of lab-scale chemical synthesis has become a driving force behind many routine, yet error-prone, reaction and synthetic procedures. These procedures include reactions involving polypeptides, RNA, DNA, proteins, carbohydrates, and other macromolecules. In many of these synthetic procedures, miniaturization and integration of unit operations enables several functions to be performed automatically in single or interconnected modules, which provide precise environmental control for each step. There is therefore a need to eliminate manual, error-prone operations in the synthesis of antibody conjugates (ACs) and to improve the quality and throughput of produced ACs through automation and integration of all synthetic steps.

For example, antibodies attached to biologically active drugs or imaging tracers present a significant source of next-generation oncolytic therapies and diagnostics with the potential to improve clinical outcomes for a diverse population of cancer patients. Other methods involving post-translational modification of antibodies include modification of the amino acids or the carbohydrates in antibodies, humanization of antibodies, dimerization or oligomerization of antibodies, and cross-linking of antibodies with other antibodies, antibody fragments, or other biologics. The growth in clinical trials, FDA-approved products, and antibody conjugate-related publications involving antibody-tracer conjugates (ATCs) and antibody-drug conjugates (ADCs), evidences the extent and promise of this research area. In this context, production and validation of new antibody conjugates (ACs) are integral to a variety of fundamental and preclinical studies. Traditional manual synthesis of ACs is labor-intensive, requires large reagent volumes, and suffers from inconsistency and poor reproducibility that can yield unacceptable proportions of false positives and false negatives in imaging studies. These deficiencies have motivated pursuit of alternative approaches to manual AC preparation including process miniaturization and automation.

Described herein is an acoustic separation device including a microfluidic device architecture that locally augments the pressure field for separation and enrichment of targeted microparticles in a longitudinal acoustic trap. Pairs of pillar arrays comprise "pseudo walls" that are oriented perpendicular to the inflow direction. Though sample flow is unimpeded, pillar arrays support half-wave resonances that correspond to the array gap width. Positive acoustic contrast particles of supracritical diameter focus to nodal locations of the acoustic field and are held against drag from the bulk fluid motion. Thus, the longitudinal standing bulk acoustic wave (LSBAW) device achieves size-selective and material-specific separation and enrichment of microparticles from a continuous sample flow. Finite element analysis models are used to predict eigenfrequencies of LSBAW architectures with two pillar geometries, slanted and lamellar. Corresponding pressure fields are used to identify longitudinal resonances that are suitable for microparticle enrichment. Optimal operating conditions exhibit maxima in the ratio of acoustic energy density in the LSBAW trap to that in inlet and outlet regions of the microchannel. Separation and isolation of 20 µm polystyrene and ~10 µm antibody-decorated glass beads within both pillar geometries is demonstrated. The results also establish several practical attributes of our approach. The LSBAW device is inherently scalable and enables continuous enrichment at a prescribed location. These features benefit separations applications while also allowing concurrent observation and analysis of trap contents. The acoustic separation device is well-suited to a range of applications, from ex vivo cancer assays and diagnostics (e.g., ELISA) to imaging (antibody-tracer conjugates) and interventions (antibody-drug conjugates).

SUMMARY

In one aspect, disclosed herein is a method for isolating mammalian cells under continuous flow conditions. The method comprises providing a plurality of mammalian cells and loading the plurality of mammalian cells into an acoustic separation device, wherein the acoustic separation device comprises: an inlet; an outlet; a channel coupled to the inlet and the outlet, wherein the channel defines a flow path between the inlet and the outlet; a standing acoustic wave generating device; and at least one pillar array comprising a plurality of pillars, wherein the at least one pillar array is situated within the flow path defined by the channel, wherein the at least one pillar array comprises a first pillar array and a second pillar array, wherein the first pillar array is substantially parallel to the second pillar array, wherein the first pillar array and the second pillar array form an enrichment structure. The method further comprises generating an augmented pressure field comprising locally augmenting, by the enrichment structure, a pressure field generated by the standing acoustic wave generating device and isolating at least one of the plurality of mammalian cells by using the augmented pressure field to facilitate retention of the at least one of the plurality of mammalian cells at a single lateral location within the flow path.

In another aspect, disclosed herein is a method for enriching mammalian cells under continuous flow conditions. The method comprises providing a plurality of mammalian cells and loading the plurality of mammalian cells into an acoustic separation device, wherein the acoustic separation device comprises: an inlet; an outlet; a channel coupled to the inlet and the outlet, wherein the channel defines a flow path between the inlet and the outlet; a standing acoustic wave generating device; and at least one pillar array comprising a plurality of pillars, wherein the at least one pillar array is situated within the flow path defined by the channel, wherein the at least one pillar array comprises a first pillar array and a second pillar array, wherein the first pillar array is substantially parallel to the second pillar array, wherein the first pillar array and the second pillar array form an enrichment structure. The method also comprises generating an augmented pressure field comprising locally augmenting, by the enrichment structure, a pressure field generated by the standing acoustic wave generating device and retaining, using the augmented pressure field, at least one of the plurality of mammalian cells at a single lateral location within the flow path. The method further comprises sequentially performing a plurality of reagent introduction and washing steps to the at least one retained mammalian cell to produce a final enriched mammalian cell product.

In yet another aspect, disclosed herein is a method for enriching microorganisms under continuous flow conditions. The method comprises providing a plurality of microorganisms and loading the plurality of microorganisms into an acoustic separation device, wherein the acoustic separation device comprises: an inlet; an outlet; a channel coupled to the inlet and the outlet, wherein the channel defines a flow path between the inlet and the outlet; a standing acoustic wave generating device; and at least one pillar array comprising a plurality of pillars, wherein the at least one pillar array is situated within the flow path defined by the channel, wherein the at least one pillar array comprises a first pillar array and a second pillar array, wherein the first pillar array is substantially parallel to the second pillar array, wherein the first pillar array and the second pillar array form an enrichment structure. The method also comprises generating an augmented pressure field comprising locally augmenting, by the enrichment structure, a pressure field generated by the standing acoustic wave generating device and retaining, using the augmented pressure field, at least one of the plurality of microorganisms at a single lateral location within the flow path. The method further comprises sequentially performing a plurality of reagent introduction and washing steps to the at least one retained microorganism to produce a final enriched microorganism product.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The embodiments described herein may be better understood by referring to the following description in conjunction with the accompanying drawings.

FIG. 6A depicts an exemplary embodiment of investigating acoustic particle focusing in 2D reservoirs that are representative of 3D Electronsonic Actuation Microarray (EAM) geometry, top view of the experimental setup used to visualize particle migration under the action of an applied acoustic field, in accordance with the present disclosure.

FIG. 6B depicts an exemplary embodiment of investigating acoustic particle focusing in 2D reservoirs that are representative of 3D Electronsonic Actuation Microarray (EAM) geometry, bottom view of the experimental setup used to visualize particle migration under the action of an applied acoustic field, in accordance with the present disclosure FIG. 6C depicts an exemplary embodiment of investigating acoustic particle focusing in 2D reservoirs that are representative of 3D Electronsonic Actuation Microarray (EAM) geometry, finite element analysis (FEA) domain used to model the acoustic response of the 2D assembly, in accordance with the present disclosure.

FIG. 8A depicts an exemplary embodiment of an Electrosonic Actuation Microarray (EAM), 3D schematic of device concept, in accordance with the present disclosure.

FIG. 8B depicts an exemplary embodiment of an Electrosonic Actuation Microarray (EAM), detail of a single nozzle illustrating resonant acoustic field focusing that drives sample ejection and mechanoporation of biological cells, in accordance with the present disclosure.

FIG. 8C depicts an exemplary embodiment of an Electrosonic Actuation Microarray (EAM), SEM image of fabricated silicon nozzle microarrays (scale bar is 300 µm), in accordance with the present disclosure.

FIG. 8D depicts an exemplary embodiment of an Electrosonic Actuation Microarray (EAM), SEM side view image of a fabricated silicon nozzle (scale bar is 100 µm), in accordance with the present disclosure.

FIG. 8E depicts an exemplary embodiment of an Electrosonic Actuation Microarray (EAM), SEM side view image of a fabricated silicon nozzle (scale bar is 25 µm), in accordance with the present disclosure.

FIG. 8F depicts an exemplary embodiment of an Electrosonic Actuation Microarray (EAM), sample ejection from an assembled prototype device, in accordance with the present disclosure.

FIG. 10A depicts an exemplary embodiment of a conceptual high-throughput acoustic particle separation method/device, in accordance with the present disclosure.

FIG. 10B depicts an exemplary embodiment of a conceptual high-throughput acoustic particle separation method/device detailing separation of larger cells from red blood cells and platelets in a spatially varying acoustic field oriented perpendicular to the direction of bulk flow, in accordance with the present disclosure.

FIG. 13A outlines LSBAW microchannel fabrication.

FIG. 13B depicts slanted pillar arrays comprising individual slanted pillars.

FIG. 13C depicts lamellar pillar arrays comprising individual lamellar pillars.

FIG. 18A depicts predicted pressure field augmentation at first and fourth enrichment structure resonances for slanted pillars.

FIG. 18B depicts LSBAW enrichment performance using slanted pillars to focus 20 µm polystyrene beads.

FIG. 18C depicts LSBAW enrichment performance using slanted pillars to focus 20 µm polystyrene beads.

FIG. 18D depicts LSBAW enrichment performance using slanted pillars to focus antibody-decorated glass spheres.

FIG. 18E depicts predicted pressure field augmentation at first and fourth enrichment structure resonances for lamellar pillars.

FIG. 18F depicts LSBAW enrichment performance using lamellar pillars to focus 20 µm polystyrene beads.

FIG. 18G depicts LSBAW enrichment performance using lamellar pillars to focus 20 µm polystyrene beads.

FIG. 18H depicts LSBAW enrichment performance using lamellar pillars to focus antibody-decorated glass spheres.

FIG. 29A depicts binding of a fluorescently labeled secondary antibody to a target cFOS-antibody.

FIG. 29B depicts a binding curve used to calculate a binding constant $K_d$.

DETAILED DESCRIPTION

Figure 1:
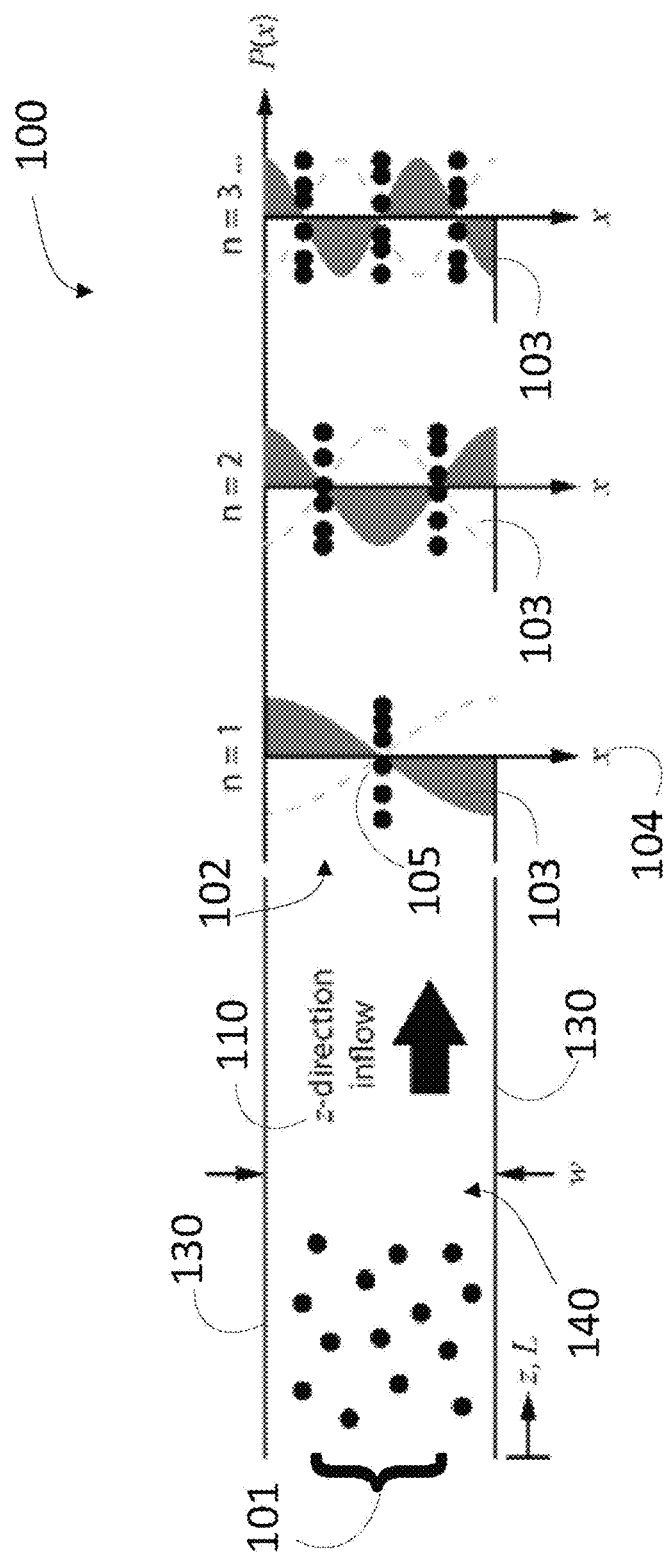
FIG. 1 depicts an exemplary embodiment of conventional microchannel acoustophoresis, in accordance with the present disclosure.

This application is generally related to subject matter disclosed in U.S. Pat. No. 10,807,029 filed Sep. 14, 2018 as a National Phase Entry of PCT Patent Application No. PCT/US2017/022484 filed Mar. 15, 2017 entitled HIGH THROUGHPUT ACOUSTIC PARTICLE SEPARATION METHODS AND DEVICES. This U.S. patent and PCT Application claim the benefit of U.S. Provisional Application No. 62/308,547 filed Mar. 15, 2016. Each of the U.S. patent, PCT Patent Application, and U.S. Provisional application are hereby incorporated by reference in their entirety for all purposes.

Embodiments provided herein introduce a platform for microfluidic manipulation, modification, and detection of macromolecule reagents and/or nanomaterials using microscale carrier particles held within an enrichment structure generated by an acoustic separation device. The enrichment structure may be located between a pair of perforated walls enhancing a local acoustic pressure field within a channel to preferentially immobilize a reagent, substrate, or a structure, from a suspension. Reagents may include macromolecules, for example DNA, RNA, carbohydrates, proteins, antibodies, viruses, or other biomolecules or macromolecules. Substrates and structures suitable for use with embodiments of the present disclosure may include microparticles, for example polymeric and/or glass beads. A pressure minimum is generated perpendicular to an inflow direction allowing contactless, sequential chemical reactions on the substrate, and can further facilitate multiple mixing, washing, buffer exchange, and release steps. The present disclosure integrates individual steps in a functional unit that may provide automated synthesis and facilitates multiple and complex chemical modifications of sensitive molecules, thus eliminating manual, error-prone operations. For example, embodiments provided herein may facilitate antibody (Ab) attachment, alteration, and release, for example from a microcarrier such as a glass or polymer bead, and biomarker detection.

Microfluidics enables non-contact, continuous-flow, and small-volume mixing, reaction, and separation of various microparticles and reagents (e.g., proteins, antibodies, RNA, DNA, carbohydrates, etc.) in solution. In conventional microscale acoustofluidic particle manipulation, particles are manipulated by traveling or standing waves (in both cases, primary acoustic radiation force (ARF) drives particle motion) or acoustic streaming (acoustic waves generate motion in a fluid, which then "pulls" particles along due to drag). The high throughput acoustophoresis device provided herein uses standing wave manipulation of particles via ARF. Acoustic radiation force (for spherical particles in standing plane waves) is directly proportional to the acoustic contrast factor (which is a function of the density and compressibility ratios of the particles and fluid). ARF is also proportional to the particle volume (or radius to the third power, $a^3$) and the acoustic energy density, $E_{ac}$, which is a function of the acoustic pressure amplitude (larger for larger pressure amplitude), and ARF is inversely proportional to the wavelength of the plane wave. For particles of different sizes and properties, the differences in the magnitude and direction of the ARF are due to the different particle sizes, densities, and compressibilities. For a given particle (fixed size and properties), the magnitude of the ARF (and thus the driving and holding force for acoustic particle separation) can be increased by increasing the frequency of the plane wave generated during operation (subject to limitations on available frequencies of operation). The magnitude of the ARF can also be increased by increasing the amplitude of the pressure field, for example, by modifying material properties of the structure to increase the acoustic impedance mismatch between the microchannel walls and the fluid. The magnitude of the ARF can also be increased by changing the geometry to enhance constructive interference of acoustic waves within the fluid. In some embodiments, the pyramidal nozzle array of an Electrosonic Actuation Microarray (EAM) may focus acoustic waves to generate a higher pressure amplitude for driving ejection of fluid. Therefore, geometry may be used to dictate frequencies of operation or to enhance the separation through geometric focusing of acoustic waves (e.g., use of various acoustic horn shapes).

Any multiple of half the wavelength λ, of a standing wave can be equated to the distance, d (i.e., (2d)/1, (2d)/2, (2d)/3 . . . ), between two surfaces (acoustic reflectors, or pseudo surfaces/acoustic reflectors). The denominator of the expression for wavelength as a function of distance is the mode, n, of the resonating geometry. The actuation frequencies, f, available to generate a standing acoustic wave between the two surfaces are then dictated by these wavelengths and the speed of sound, c, within the fluid as f=c/λ=n c/(2 d).

Typical separations are performed in water or water-like fluids, or blood and blood-like fluids with c~1500 m/s. The threshold frequency for microfluidic separation of a 10 µm particle (representative of cells, cell-like objects, and hollow glass spheres) in water is about 1 MHz. Below 1 MHz, the ARF may be not large enough to overcome viscous drag (which acts against ARF), and particles move only very slowly toward nodes/antinodes of the acoustic field. For smaller particles, higher frequency pressure fields are required to effect good focusing; however, high frequency (short wavelength) acoustic waves are subject to significant attenuation over short distances. For example, the larger the number of wavelengths of an acoustic field present between the geometric boundaries (walls) of a microchannel, the greater the attenuation of the amplitude of the pressure wave, which leads to a decrease in the ARF. For this reason, the number of wavelengths (mode number) of the acoustic field is typically limited to less than about 3 wavelengths. For cell-like objects suspended in water-like fluids, separations are typically carried out in the frequency range of about 1 MHz to about 20 MHz, which corresponds to a first mode half-wavelength of about 0.04-0.75-mm, or if limited to n<6, d must be less than approximately 0.25 to 4.5 mm. Separation of larger particles or particles with larger acoustic contrast may be performed with larger inter-reflector distances at lower frequencies. However, separation may be less effective for distances of above 10 mm in width or below 100 kHz for any particles of interest. The minimum distance between reflectors is based on attenuation in the fluid, but also on the size of the particles to be separated. In general, the wavelength of the acoustic field should be "large" (>about 5-10 times the diameter of a particle, a) compared to the size of the particles, so use of inter-reflector distances of less than half of 10a or 50 μm for 10 μm diameter particles may be less effective.

As shown in FIG. 1, conventional separations may be performed by a acoustic separation device 100 comprising single or parallel arrays of two-dimensional microchannels 140 supporting a bulk inflow in a z-direction. Suspended particles 101 enter a focusing/separation zone 102 where a standing acoustic field comprising standing acoustic waves 103 is oriented non-parallel to the flow between the walls 130 of the microchannel. In the illustrated embodiment, the standing acoustic field is oriented perpendicular to the flow in the x-direction 104. In general, any mode of the acoustic field can be used subject to the limitations described above. As particles 101 flow along the acoustically active zone 102, they gradually migrate to nodes/antinodes 105 (depending on positive/negative acoustic contrast of the particles) of the standing acoustic wave 103. The number of nodes/antinodes can be any positive integer n. In the illustrated embodiment, standing acoustic waves 103 comprising n=1, n=2, and n=3 nodes/antinodes are illustrated.

The time required to adequately focus a given particle 101 is dependent upon the magnitude of the ARF, and the particle location relative to the node/antinode 105 of the field when it enters the acoustically active zone 102. The residence time of the particle is equal to the length of the channel divided by the flow velocity. If the residence time is not greater than the time required to adequately focus a given particle, the particle 101 will not be separated from the bulk flow 110. For this reason, if the ARF is not large enough, due to low frequency operation, low pressure wave amplitude, small particle diameter, or small acoustic contrast, the channel is not long enough, or the flow rate is too high, a given acoustic separation device 100 will not be able to adequately separate a heterogeneous particle suspension 101. Thus, for particles with 101 smaller differences in acoustic contrast and size, a given acoustic separation device 100 may need a lower flow rate (limiting throughput) or an unreasonably long channel.

High throughput separations can be achieved by orienting the acoustic field parallel to the direction of flow or at least not perpendicular to the direction of flow (FIGS. 2-6). In this way, all suspended particles 101 must flow through the nodes/antinodes 105 of the acoustic field during a spatial distance on the order of that of the wavelength of the acoustic field.

Figure 2:
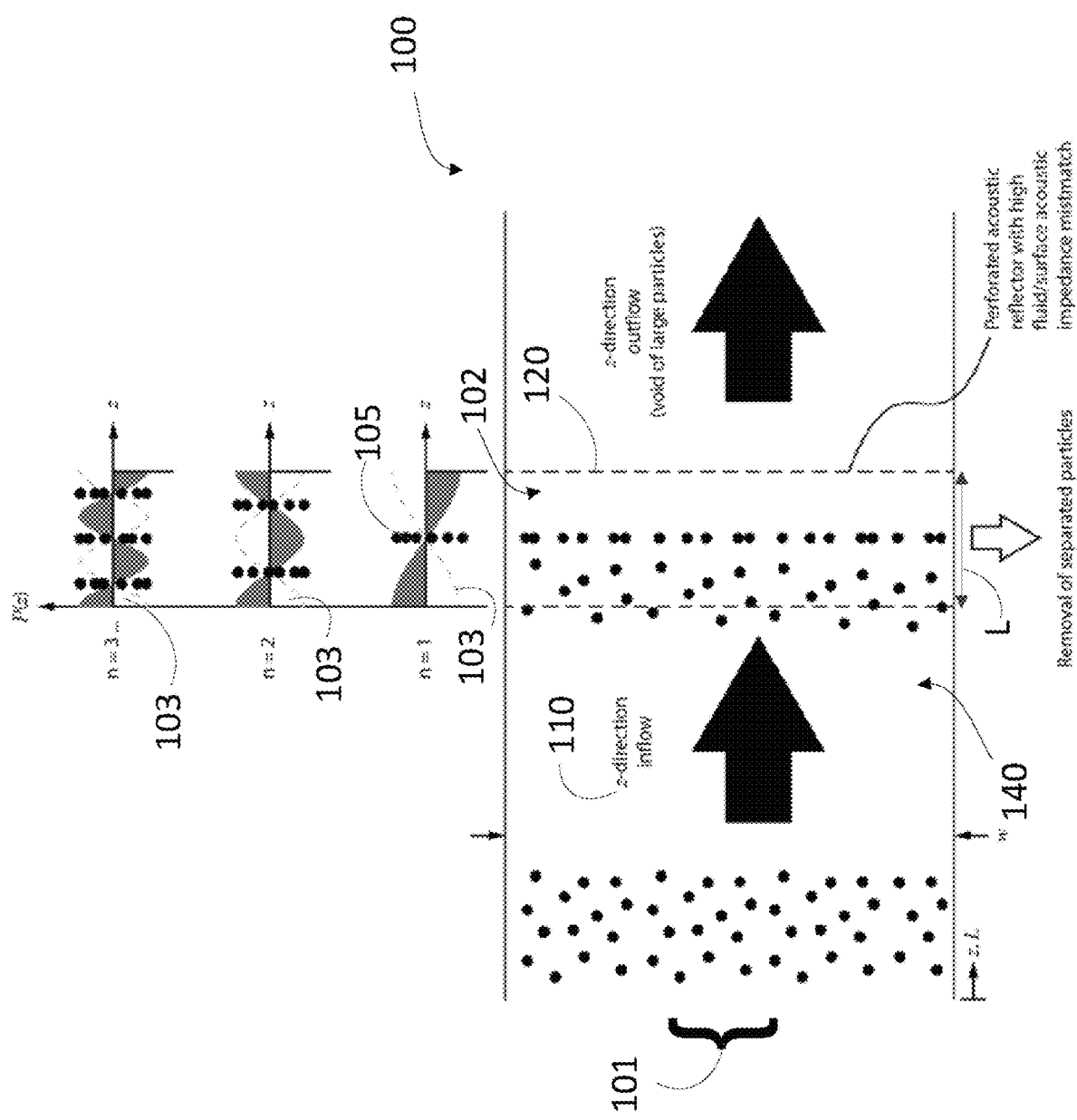
FIG. 2 depicts an exemplary embodiment of a system that can perform high throughput acoustophoresis, in accordance with the present disclosure.
Figure 3:
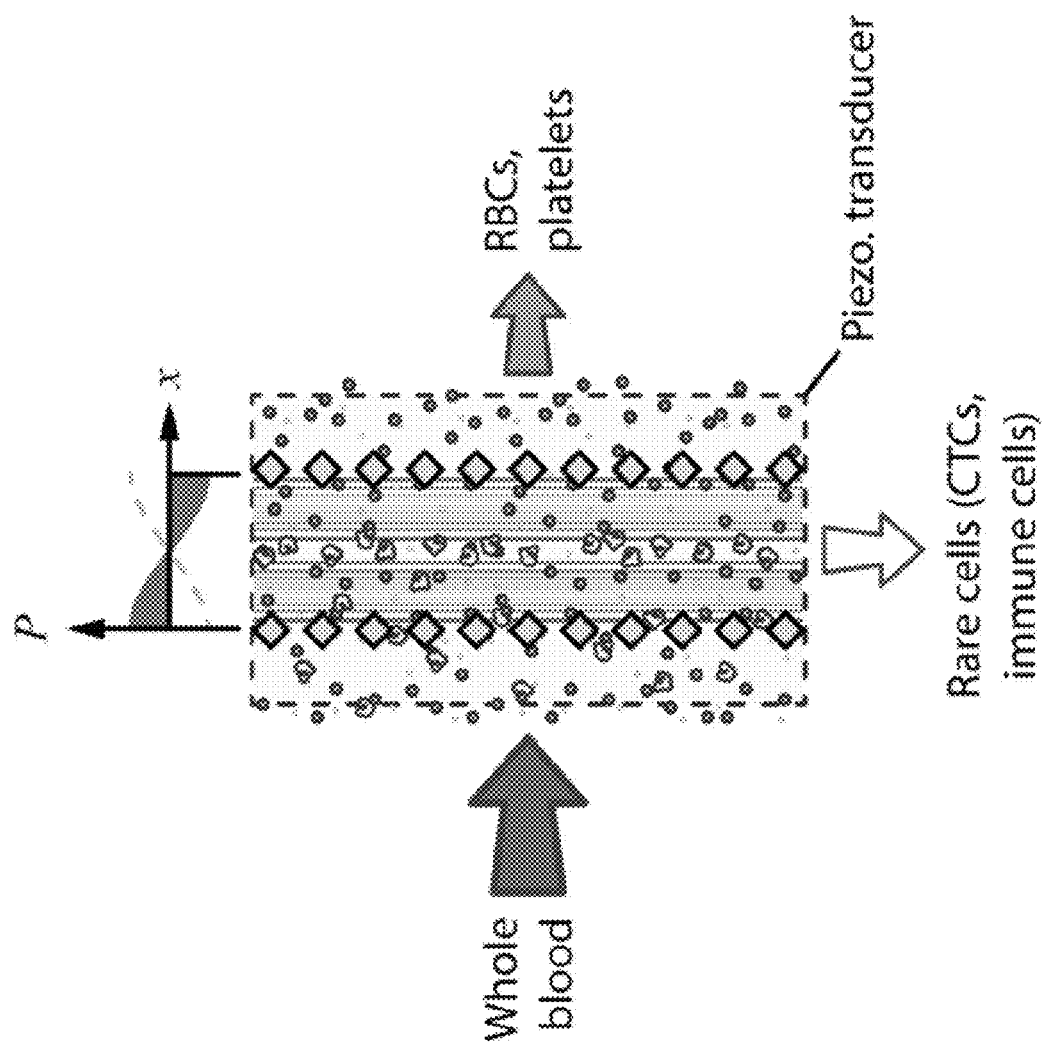
FIG. 3 depicts an exemplary embodiment of particle/cell focusing between two perforated walls where the overall flow is to the right (horizontal). The field sets up nodal/antinodal lines (planes) in the vertical direction, in accordance with the present disclosure.

As shown in FIG. 2, an acoustic field is maintained between perforated reflector walls 120 made of materials with substantially higher acoustic impedance as compared to the fluid. Perforations in reflector walls 120 allow suspended particles to flow through while not significantly affecting the acoustic field structure or strength. The strength of the ARF during transit through the focusing/separation zone 102 can be increased by decreasing the distance L between reflectors 120 (i.e., by allowing operation at higher frequencies). Indeed, an acoustic separation device 100 may contain a series of reflector pairs 120 of different spacing L to allow separation of a heterogeneous suspension into its various constituent particles. For example, for whole blood, large white blood cells may be separated by widely spaced reflectors and red blood cells may be separated by closely spaced reflectors, as illustrated in FIG. 3.

With further reference to FIG. 2, because the acoustic field is oriented parallel (or at least non-perpendicular) to the direction of flow 110, a width, w, of the microchannel 140 (and therefore its cross-sectional area, $A_c$, can be increased without affecting the frequency of operation. This allows for increased throughput at a given flow velocity, v (flow rate, $Q=vA_c$) or for increased flow rate since pressure drop at a given flow rate will be less (assuming that ARF is still strong enough to overcome drag and to focus particles). If needed, removal of separated particles 101 may be performed in sequential steps where separation is followed by flow in an orthogonal direction. Alternatively, a downstream valve (not shown) allows separated species confined between perforated reflector walls 120 to be released with flow in the normal outflow direction for collection in a separate reservoir (not shown).

Figure 4:
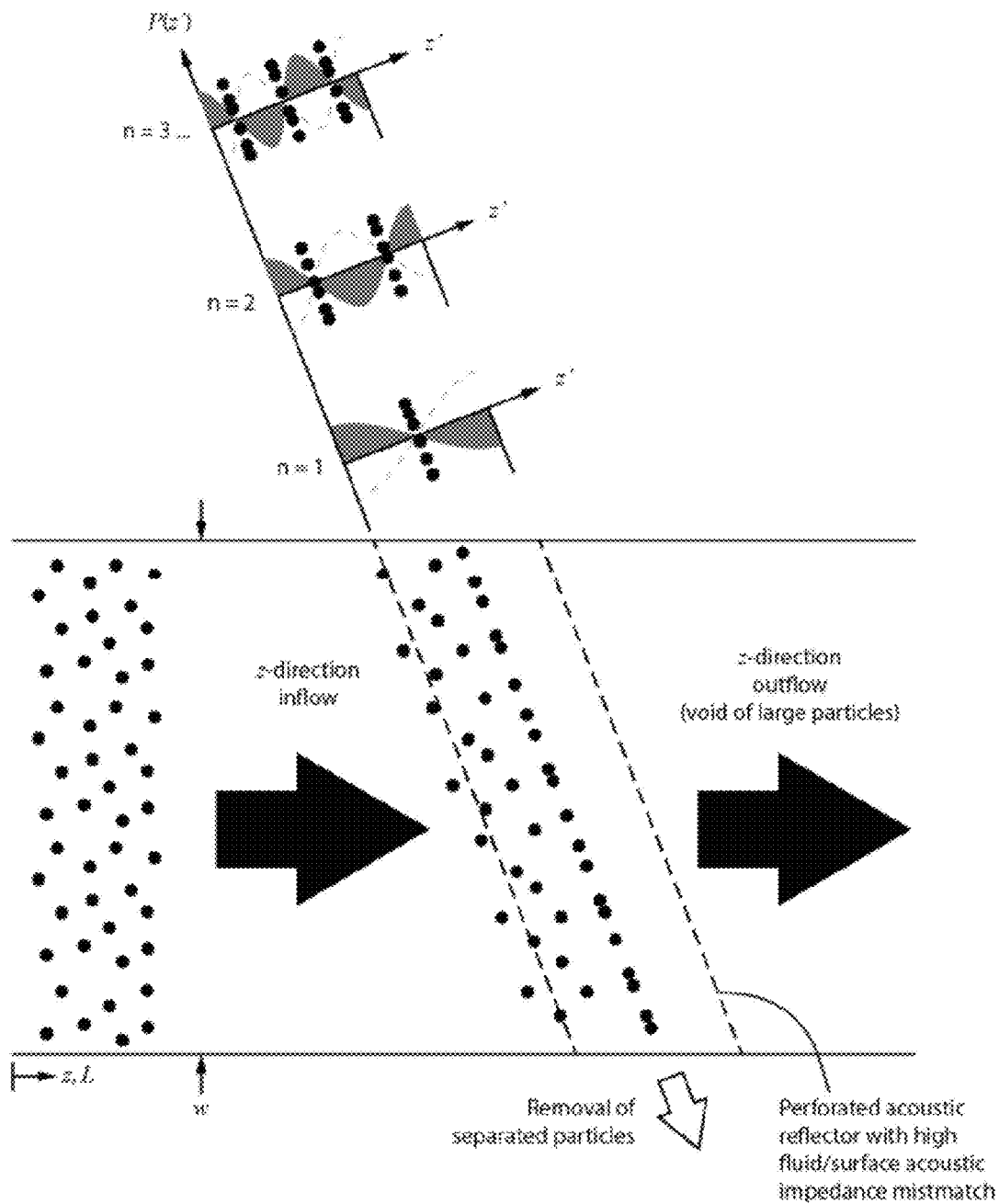
FIG. 4 depicts an acoustic field oriented not perpendicular to the direction of flow.

As shown in FIG. 4, in some embodiments, the acoustic field is oriented at an angel such that acoustic field is neither parallel nor perpendicular to the direction of flow.

Figure 5:
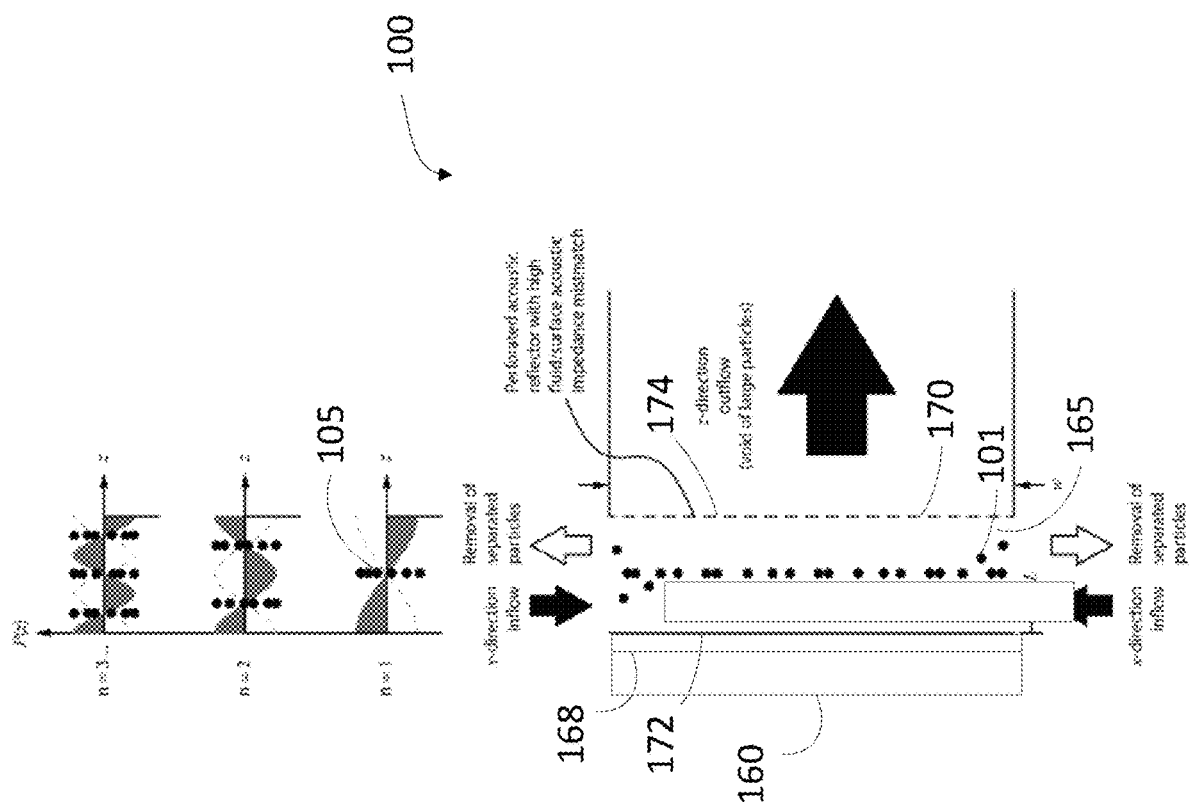
FIG. 5 depicts another exemplary embodiment of a system that can perform high throughput acoustophoresis, in accordance with the present disclosure.

As shown in FIG. 5, the high throughput acoustic separation device 100 may include an actuator component 160 and a channel or reservoir 165. In the illustrated embodiment, the actuator component 160 and the channel or reservoir 165 are separated by an isolation layer 168. In some embodiments, the channel or reservoir 165 may have high acoustic impedance relative to the fluid and may be of suitable geometric arrangement for the development/maintenance of a standing pressure field that allows for trapping suspended particles 101. The actuator component 160 may generate a standing pressure field. In some embodiments, the actuator component 160 may generate an ultrasonic wave. The actuator may include, but is not limited to, a piezoelectric actuator, a capacitive actuator, or an array of interdigitated electrodes.

In some embodiments, the reservoir 165 may include an array of openings 170 on a side opposite to the actuator 160. In some embodiments, nodal/antinodal planes 105 may be established between solid 172 and/or perforated surfaces 174 in the reservoir 165. For example, a surface of the actuator 160 may be the solid surface 172 and a nozzle array may be the perforated surface 174. The actuator component 160 may include a piezoelectric transducer in some embodiments.

Flow may be driven by any source of pressure differential including, but not limited to an acoustic pressure source such as an ultrasound transducer, a pressure pump, a gas cylinder, a compressor, a vacuum pump, a syringe (manual or syringe pump), a peristaltic pump, a pipette, a piston, a capillary actor, any mechanical device, and gravity. It is not necessary that the fluid motion is driven by acoustic waves. In some embodiments, fluid may be pumped through the orifices of the nozzle plate using pressure; however, the reflectors (1 solid and 1 perforated pseudo wall) need to meet the requirements provided herein. In some embodiments, the device may include two perforated reflectors, and may not have limitations on flow rate.

As shown in FIG. 6, the actuator component 160 may comprise one or more acoustic coupling layers adjacent to the isolation layer. In some embodiments, the acoustic coupling layer may be an aluminum coupling layer. In some embodiments, the isolation layer may be a silicon isolation layer. In some embodiments, the high throughput acoustic separation device 100 may be similar to the EAM devices shown in FIGS. 8, 10 and 11.

In general, the material of the acoustic coupling layer and any isolation layers should have a low ultrasonic acoustic attenuation. The coupling layer and isolation layers may be made of materials such as, but not limited to, single crystal silicon (e.g., oriented in the (100), (110), or (111) direction), metals (e.g., aluminum, copper, stainless steel and/or brass), plastics, silicon oxide, quartz, glass, silicon nitride, and combinations thereof.

In general, the material that the channel structure is made of may have substantially higher acoustic impedance as compared to the fluid. The channel may be made of materials such as, but not limited to, single crystal silicon (e.g., oriented in the (100), (110), or (111) direction), metals (e.g., aluminum, copper, stainless steel and/or brass), plastics, silicon oxide, quartz, glass, silicon nitride, and combinations thereof.

Investigations were conducted of particle focusing in EAM-like geometries using a simplified 2D model and microfluidic chips that allowed visualization of particle migration under the action of an applied acoustic field. The acoustic simulation package of the commercial software ANSYS was used to predict how geometric parameters and material properties affect focusing performance.

Single inlet, single outlet reservoirs designed to represent cross-sections of an injection-molded EAM cartridge were micro-machined into silicon and bonded to glass providing visual access to the "ejection" chamber (see experimental setup, FIGS. 6A and 6B). Nozzle tips were left closed to facilitate filling and testing of the device. While the acoustic response of a sealed cavity differs slightly from that of a reservoir with open orifices, these differences were not expected to significantly alter conclusions related to particle focusing behavior. The ANSYS simulation domain is shown in FIG. 6C. The listed component dimensions represent combinations of piezoelectric transducer thickness $t_{pz}$ (1.5 and 2.0 mm), aluminum coupling layer thickness $t_{al}$ (2.5, 3.0 and 3.5 mm), silicon isolation layer height $h_{si}$ (0.5, 1.0 and 2.0 mm), and reservoir height from the edge of the isolation layer to the nozzle base $h_{rs}$ (500 and 900 µm), which were available for experimental evaluation; however, the model is not limited to these component dimensions.

Figure 7:
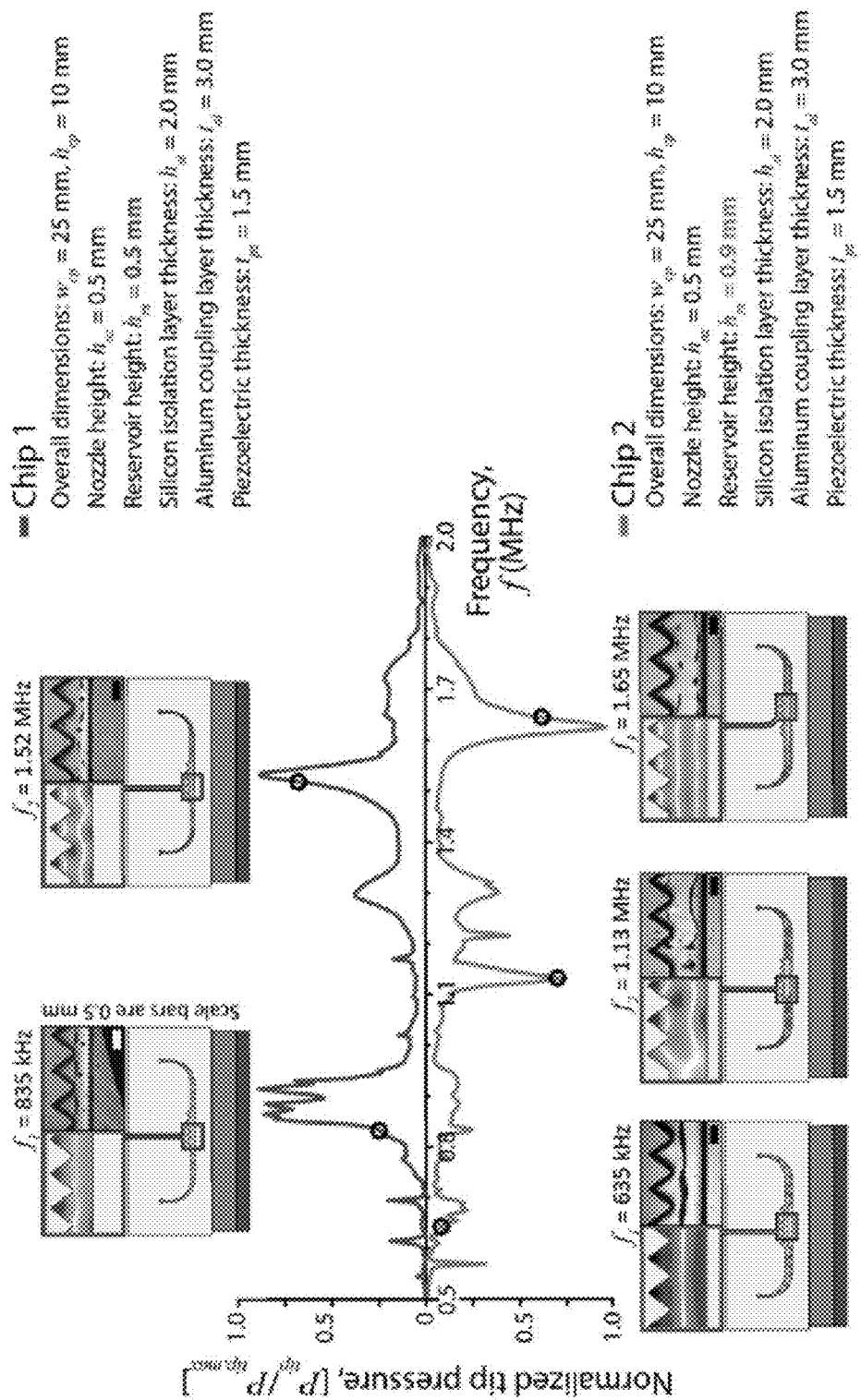
FIG. 7 depicts an exemplary embodiment of particle focusing in 2D reservoirs: tip pressure as a function of frequency is plotted for two different chip geometries, 500 µm reservoir height (Chip 1, top) and 900 µm reservoir height (Chip 2, bottom), in accordance with the present disclosure. Nodes are shown as lighter (white) and antinodes are shown as darker (black). Comparisons of predicted and observed terminal particle distributions are shown at resonant frequencies corresponding to ejection from the 3D Electronsonic Actuation Microarray (EAM).

The ANSYS model was used to predict focusing behavior for thirty six cases covering the combinations of geometric parameters listed in FIG. 6C. Chips with two different reservoir heights ($h_{rs}$=0.5 and 0.9 mm) were loaded with suspensions of 10 µm diameter polystyrene beads (density, $\rho$=1.06 g cm$^{-3}$) and driven over a range of operating frequencies from 0.5 to 2.0 MHz. For conditions exhibiting intense particle activity, images were recorded after providing sufficient time to achieve a steady-state (terminal) particle distribution. While predictions were consistent with an existing understanding of EAM operation, the model demonstrated a remarkable ability to capture all details of the final particle distributions within different reservoir geometries. As expected, particles focused at the zero pressure nodes of the standing acoustic field when driven at frequencies corresponding to half-wave resonances of the fluid-filled reservoirs (see FIG. 7). The top line in FIG. 7 is a plot of normalized tip pressure as a function of frequency for Chip 1, a 0.5 mm reservoir; the bottom line is a plot of normalized tip pressure as a function of frequency for Chip 2, a 0.9 mm reservoir. Comparisons of predicted (ANSYS FEA) and observed terminal particle distributions at resonant frequencies corresponding to ejection from the 3D EAM (and falling within the 0.5 to 2.0 MHz frequency window) are also shown. The upper row of FIG. 7 shows the first two modes of a 0.5 mm reservoir, and the lower row the first three modes of a 0.9 mm reservoir. These results demonstrate the power of a combined modeling and visualization approach to studying the acoustophoretic separations process.

As shown in FIG. 8 the actuator component 160 include a piezoelectric transducer and may produce a resonant ultrasonic wave within the reservoir and fluid. The resonant ultrasonic wave couples to and transmits through the liquid and is focused by ejector structures. The high-pressure gradient accelerates fluid out of the ejector structure to produce droplets. The droplets are produced due to break up of a continuous jet or discretely in a drop-on-demand manner. The frequency at which the droplets are formed is a function of the drive cycle applied to the actuators as well as the fluid, reservoir and ejector structure, and the ejector nozzle.

An alternating voltage is applied to the actuator to cause the actuator to produce the resonant ultrasonic wave. The actuator can operate at about 100 kHz to 100 MHz, 500 kHz to 15 MHz, and 800 kHz to 5 MHz. A direct current (DC) bias voltage can also be applied to the actuator in addition to the alternating voltage. In embodiments where the actuator is piezoelectric, this bias voltage can be used to prevent depolarization of the actuator and can also generate an optimum ambient pressure in the reservoir. In embodiments where the actuator is electrostatic, the bias voltage is needed for efficient and linear operation of the actuator. Operation of the actuator is optimized within these frequency ranges in order to match the cavity resonances, and depends on the dimensions of and the materials used for fabrication of the reservoirs and the array structure as well the acoustic properties of the operating fluid.

The dimensions of the coupling and isolation layers, if present, are chosen such that the thicknesses of the coupling and isolation layers are approximately multiples of half the wavelengths of longitudinal waves in the coupling and isolation layers at the frequency of operation. Therefore for typical coupling materials like quartz, aluminum and silicon, the dimensions of the coupling and isolation layers are from 100 micrometers to 50 centimeters in width, 10 micrometers to 50 centimeters in thickness, and 100 micrometers to 50 centimeters in length. In addition, the dimensions of the coupling and isolation layers are from 100 micrometers to 2 centimeters in width, 10 micrometers to 10 millimeters in thickness, and 100 micrometers to 2 centimeters in length. Further, the dimensions of the coupling and isolation layers are from 100 micrometers to 1 centimeters in width, 10 micrometers to 2 millimeters in thickness, and 100 micrometers to 1 centimeter in length.

The dimensions of the actuator may depend on the type of actuator used. In some embodiments, where the actuator is a piezoelectric actuator, the thickness of the actuator is determined, at least in part, by the frequency of operation and the type of the piezoelectric material. The thickness of the piezoelectric actuator is chosen such that the thickness of the actuator is about half the wavelength of longitudinal waves in the piezoelectric material at the frequency of operation. Therefore, in the case of a piezoelectric actuator, the dimensions of the actuator are from 100 micrometers to 10 centimeters in width, 10 micrometers to 1 centimeter in thickness, and 100 micrometers to 10 centimeters in length. In addition, the dimensions of the actuator are from 100 micrometers to 2 centimeters in width, 10 micrometers to 5 millimeters in thickness, and 100 micrometers to 2 centimeters in length. Further, the dimensions of the actuator are from 100 micrometers to 1 centimeters in width, 10 micrometers to 2 millimeters in thickness, and 100 micrometers to 1 centimeter in length.

Figure 9:
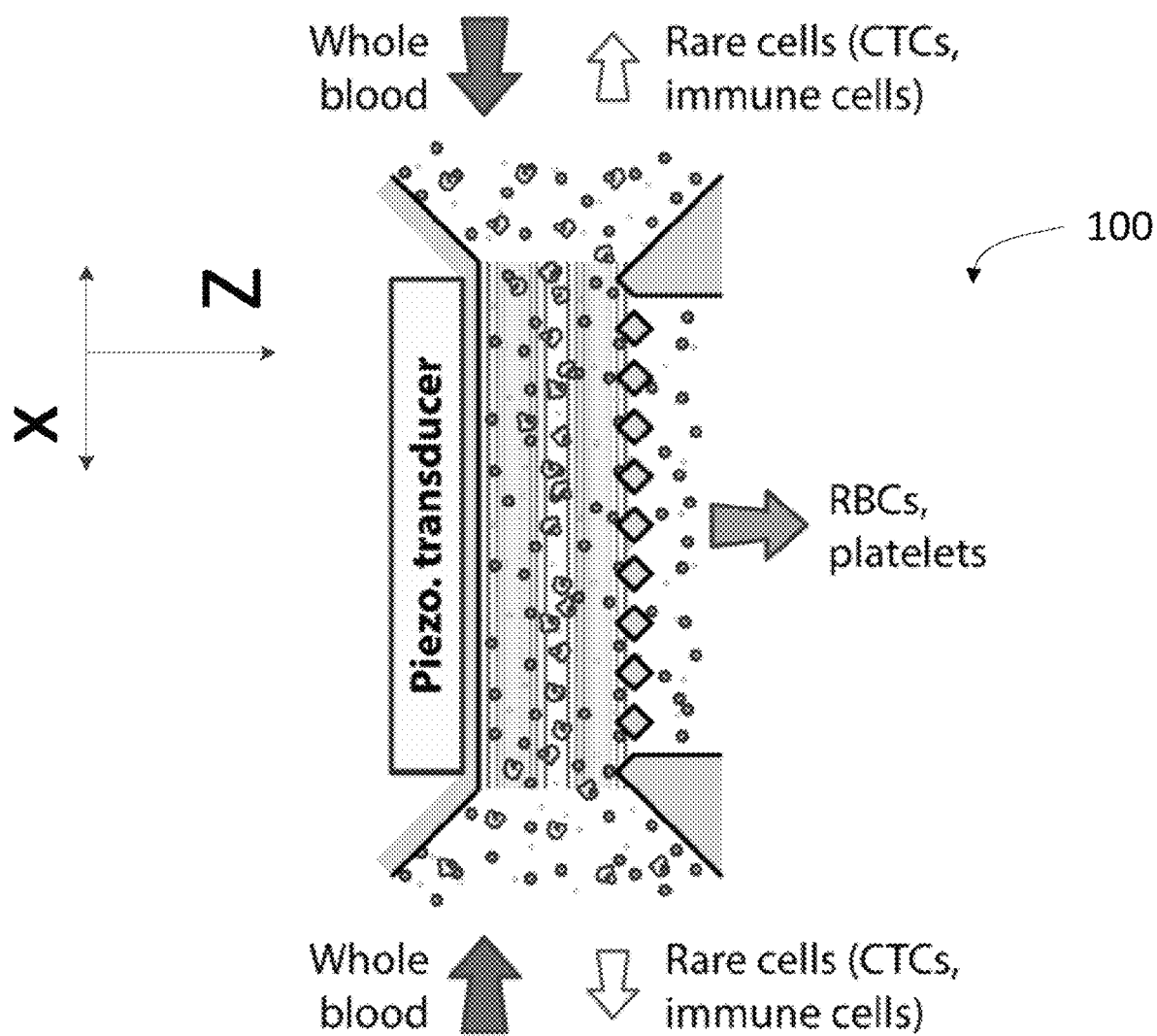
FIG. 9 depicts an exemplary embodiment of particle/cell focusing between one solid and one perforated wall where overall flow enters at the top and bottom and flows to the right (horizontal), but the field sets up nodal/antinodal lines (planes) in the vertical direction, in accordance with the present disclosure.

As shown in FIG. 9, high-throughput separations may be performed in a reflector arrangement where one of the perforated reflectors may be replaced by a solid reflector. In the illustrated embodiment, the solid reflector is associated with a surface of a piezoelectric transducer. A heterogeneous particle suspension comprising whole blood may enter in the x-direction at the top and bottom of the acoustically active zone and exit to the right after particle separation and focusing in the z-direction. One embodiment of this arrangement may be an ultrasonic droplet generator, as shown in FIG. 8.

In the embodiment illustrated in FIG. 9, the high throughput microfluidic device 100 may be used for isolation of rare cells from whole blood. Under an operating frequency of about 1 MHz, the particle size threshold for effective separation is ~10 μm (diameter) as the primary acoustic radiation force scales with the cube of the particle radius. Particles of smaller diameter (e.g., red blood cells (RBCs) and platelets) may be unaffected by the acoustic field, passing unimpeded through the sample reservoir and exiting from the nozzle orifices. In some embodiments, there may be preferential recovery of polystyrene beads with a diameter of about 5 μm (~100%) versus about 10 μm (<40%) during EAM ejection of a heterogeneous bead mixture. Isolation of specific targeted immune cells from a white blood cell population, where size differentials are less pronounced, may require characterization and optimization of EAM operating parameters. In some embodiments, separating particles with similar acoustic contrast may require sequential separation in the high throughput acoustophoresis device. Due to the inherent scalability of the planar microarray format, the three-dimensional (3D) high throughput acoustophoresis device addresses throughput limitations of traditional 2D microchannel acoustophoresis devices, not only enabling use of acoustic separations in a diagnostic tool, but enabling therapeutic applications where high-throughput separation is essential.

The high throughput microfluidic device 100 may be used for isolation of particles, microorganisms, and/or cells including, but not limited to immune cells, circulating tumor cells (CTCs), bacterial cells, macromolecules, nanoparticles, viruses, microparticles (glass, polymeric, metallic, etc.), or any mammalian or non-mammalian cell. The high throughput microfluidics device 100 may be used for isolation of macromolecules, for example DNA, RNA, carbohydrates, proteins, antibodies, viruses, or other biomolecules or macromolecules. In some embodiments, the high throughput microfluidics device 100 may isolate cells with relatively low abundance from whole blood or other bodily fluids. The standing pressure field formed in the sample reservoir at particular resonant frequencies is also conducive to separation and isolation of cell-sized (~1-50 μm) and sub-cellular (<1 μm) particles. In some embodiments, the resonant frequency may be 0.1 to 100 MHz. Stratification of nodal (zero pressure) and antinodal (maximum pressure amplitude) planes perpendicular, or at least not parallel, to the direction of bulk flow (i.e., the direction of sample ejection from the orifices of the microarray or generally outflow from the device) offers a means of preferentially focusing (and thus retaining) objects of a particular size, shape, density or compressibility from a larger population of objects.

An embodiment of a high-throughput microfluidics device is shown in FIG. 10. In this embodiment, there is an array of pyramidal nozzles from which a sample is ejected.

FIG. 10B shows a plot of the pressure field within the chamber showing the two nodal planes where cells will focus. One antinode is located at the piezoelectric surface, and another antinode is located in the "middle" of the chamber. The final antinode is the pressure field focal point in the pyramidal nozzles, which is what drives ejection. That focal point dictates the "effective" height of the chamber. The distance between the piezoelectric surface and the pressure field focal point defines the dimension over which an acoustic wave is "standing". For example, for FIG. 10, there are 2 half-wavelengths of the field located between those two points. That represents the second half-wavelength resonance for the device. There are two nodes for focusing at this frequency. If the device were driven at a lower resonant mode, there would only be two antinodes and a single nodal plane for particle focusing.

Figure 11:
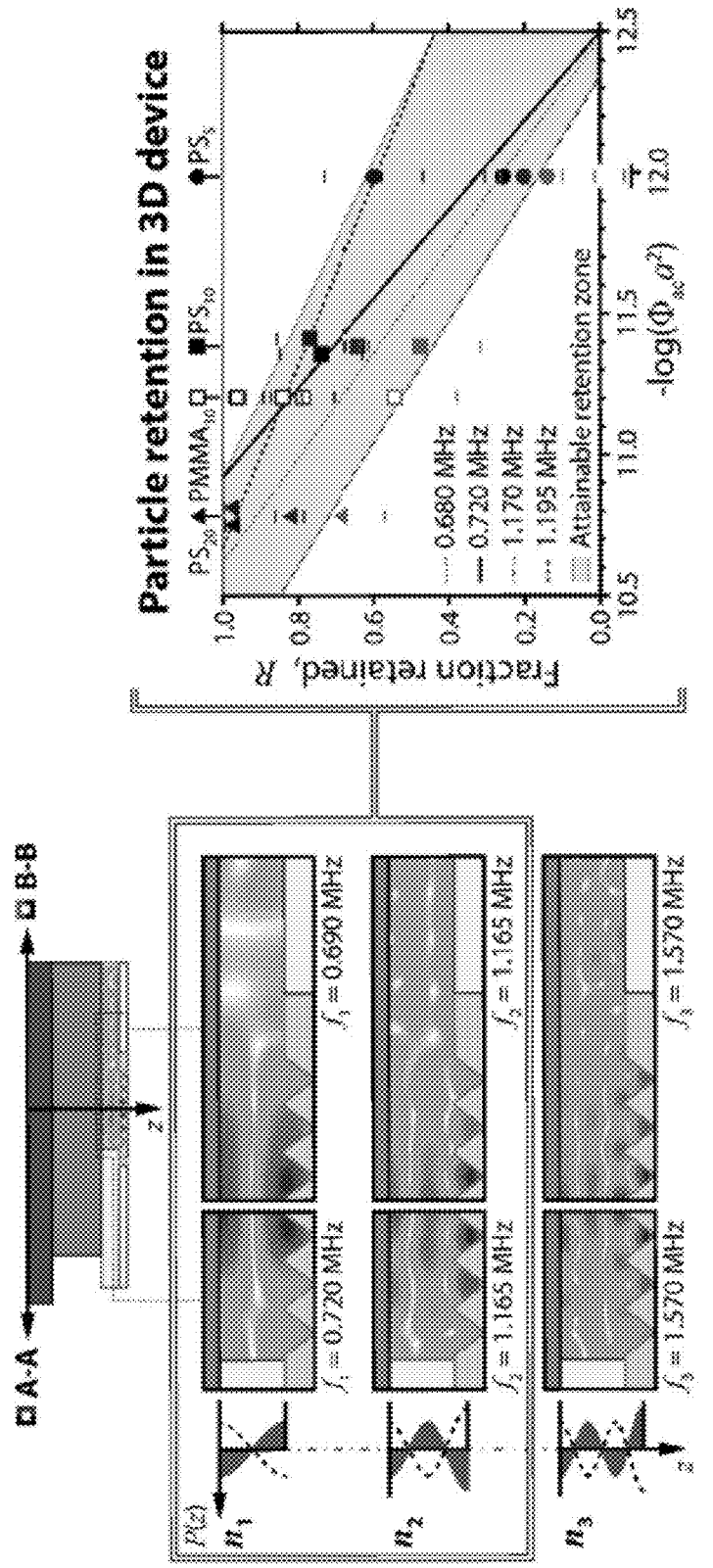
FIG. 11 depicts an exemplary embodiment of 3D Electronsonic Actuation Microarray (EAM) particle focusing modes and a plot of particles retained (y-axis) vs. acoustic focusing factor (x-axis) in accordance with the present disclosure. Nodes are shown as lighter (white) and antinodes are shown as darker (black).

FIG. 11 demonstrates preferential separation of a population of beads (5, 10, and 20 micron diameter) using a device similar to the one depicted in FIG. 10. FIG. 11 shows a plot of particles retained (y-axis) vs. acoustic focusing factor (some function of the acoustic contrast phi which is a function of density and compressibility ratios of particles to fluid) and particle size (radius, a, squared) for PS (polystyrene) and PMMA (poly(methyl methacrylate)) beads of various sizes. The PS and PMMA have different acoustic contrast due to their different material properties so a higher fraction of 10 micron PMMA particles is retained than the same size PS. The difference in retention of the three PS sizes may be purely a function of size. Various frequencies used for separation play a role in observed values. Spraying efficiency may vary at different frequencies. Accordingly, differences in behavior may be due to potential differences in acoustic behavior and definite differences in flow and drag on the particles. Nodes are shown as lighter (white) and antinodes are shown as darker (black).

Figures 12A, 12B:
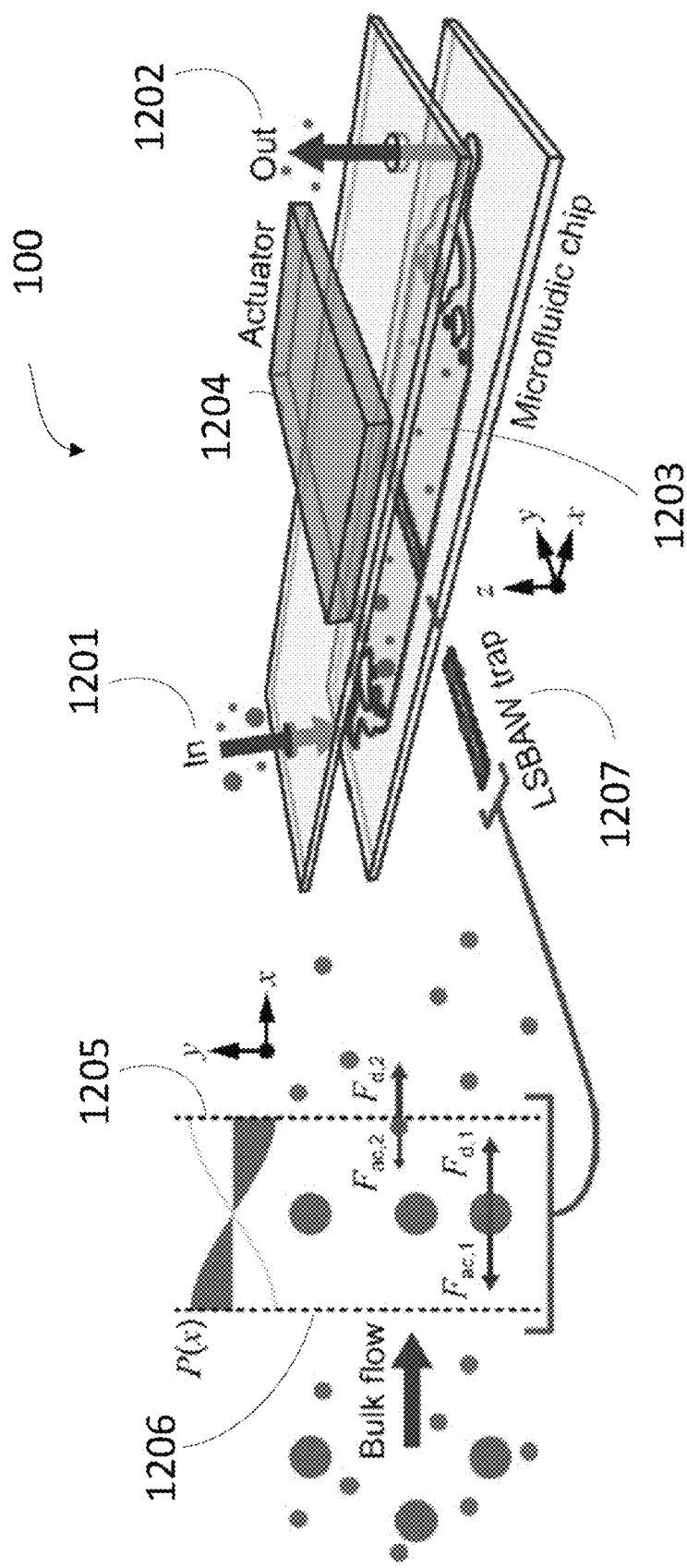
FIG. 12A depicts a longitudinal standing bulk acoustic wave (LSBAW) structure, trap, or enrichment structure that locally augments a pressure field to retain particles at a single predefined location along a channel.
FIG. 12B depicts a heterogeneous mixture is introduced into a microchannel at an inlet, and when actuated at specific resonant frequencies of the enrichment structure, target particles or reagents are separated from the channel effluent.

As shown in FIGS. 12A and 12B, the acoustic separation device 100 may incorporate an inlet 1201, and outlet 1202, and a channel 1203 coupled to the inlet and the outlet. The channel 1203 further defines a flow path between the inlet 1201 and the outlet 1202. In the illustrated embodiment, the acoustic separation device 100 further includes a standing acoustic wave generating device 1204. In the illustrated embodiment, the wave generating device 1204 includes an actuator.

The acoustic separation device 100 may further includes at least one pillar array 1205 situated within the flow path and oriented perpendicular to the inflow direction. In the illustrated embodiment, the at least one pillar array comprises a first pillar array and a second pillar array 1206. In the illustrated embodiment, the first pillar array 1205 is substantially parallel to the second pillar array 1206 and form a longitudinal standing bulk acoustic wave (LSBAW) structure, trap, or enrichment structure 1207 that locally augments a pressure field to retain particles at a single predefined location along the channel, as shown in FIG. 12A. A heterogeneous mixture is introduced into a microchannel at an inlet, and when actuated at specific resonant frequencies of the enrichment structure, target particles or reagents are separated from the channel effluent, as illustrated in FIG. 12A. After sufficient enrichment, the channel may be flushed to remove remaining non-target particles, acoustic excitation within the fluid chamber is removed, and isolated particles, structures, or reagents may be recovered. In some embodiments, the separation device 100 illustrated in FIG. 12 may be disposable.

As shown in FIGS. 13B and 13C, the pillar arrays may comprise a plurality of slanted pillars 1302 (P1, angle of inclination relative to the flow path $\theta_p=75°$) and lamellar pillars 1304 (P2, $\theta_p=90°$). In the illustrated embodiment, the slanted pillars 1302 have an angle of inclination relative to the flow path $\theta_p=75°$ In other embodiments, the slanted pillars 1302 have an angle of inclination relative to the flow path between 65° and 85°.

As shown in FIG. 13B, the average distance $L_x$ between the first and second slanted pillar arrays is 1.5 mm. In other embodiments, $L_x$ is between 0.25 and 2.5 mm.

As shown in FIG. 13C, the average distance $L_{x1}$ between the first and second lamellar pillar arrays is 1.25 mm. In other embodiments, $L_{x1}$ is between 0.25 and 2.5 mm.

As shown in FIG. 13B, the slanted pillar arrays comprise individual slanted pillars 1306 comprising a first side with a first thickness $l_p$ of 950 μm and a second side with a second thickness $t_p$ of 50 μm. In the illustrated embodiment, the ratio of the second thickness to the first thickness is about 0.05. In other embodiments, the ratio of the second thickness to the first thickness is between 0.01 and 0.9.

As shown in FIG. 13C, the lamellar pillar arrays comprise individual lamellar pillars 1308 comprising a first side with a first thickness $l_p$ of 500 μm and a second side with a second thickness $t_p$ of 50 μm. In the illustrated embodiment, the ratio of the second thickness to the first thickness is about 0.1. In other embodiments, the ratio of the second thickness to the first thickness is between 0.01 and 0.9.

In the illustrated embodiment, the lateral distance $L_{x2}$ between individual lamellar pillars 1308 in a given lamellar pillar array 1304 is 250 μm. In other embodiments, the lateral distance $L_{x2}$ between individual lamellar pillars 1308 in a given lamellar pillar array 1304 is between 50 μm and 1000 μm.

Pillars may be designed to support a node at approximately 500 kHz (gap width, $L_x$, $L_{x1}$=1.25-1.5 mm). In the illustrated embodiment, the LSBAW microchannels were fabricated in 1.5-mm thick soda/chromium blanks precoated with positive photoresist (5300 Å AZ1500, Telic Co.) as outlined in FIG. 13A. Patterned features were isotropically etched to a depth of ~60 μm using 49% (w/w) HF:69% (w/w) $HNO_3$:deionized (DI) water at a ratio of 2:1:6. Channels were enclosed via calcium-assisted glass-glass bonding of a second glass blank into which 1-mm diameter inlet and outlet holes had been drilled. A 24 mm×28 mm×1.5-mm thick PZT-8 piezoelectric transducer (APC 880, American Piezo Ceramics, Inc.) was clamped to the top side of the LSBAW chips using water as an acoustic coupling medium.

Figure 14:
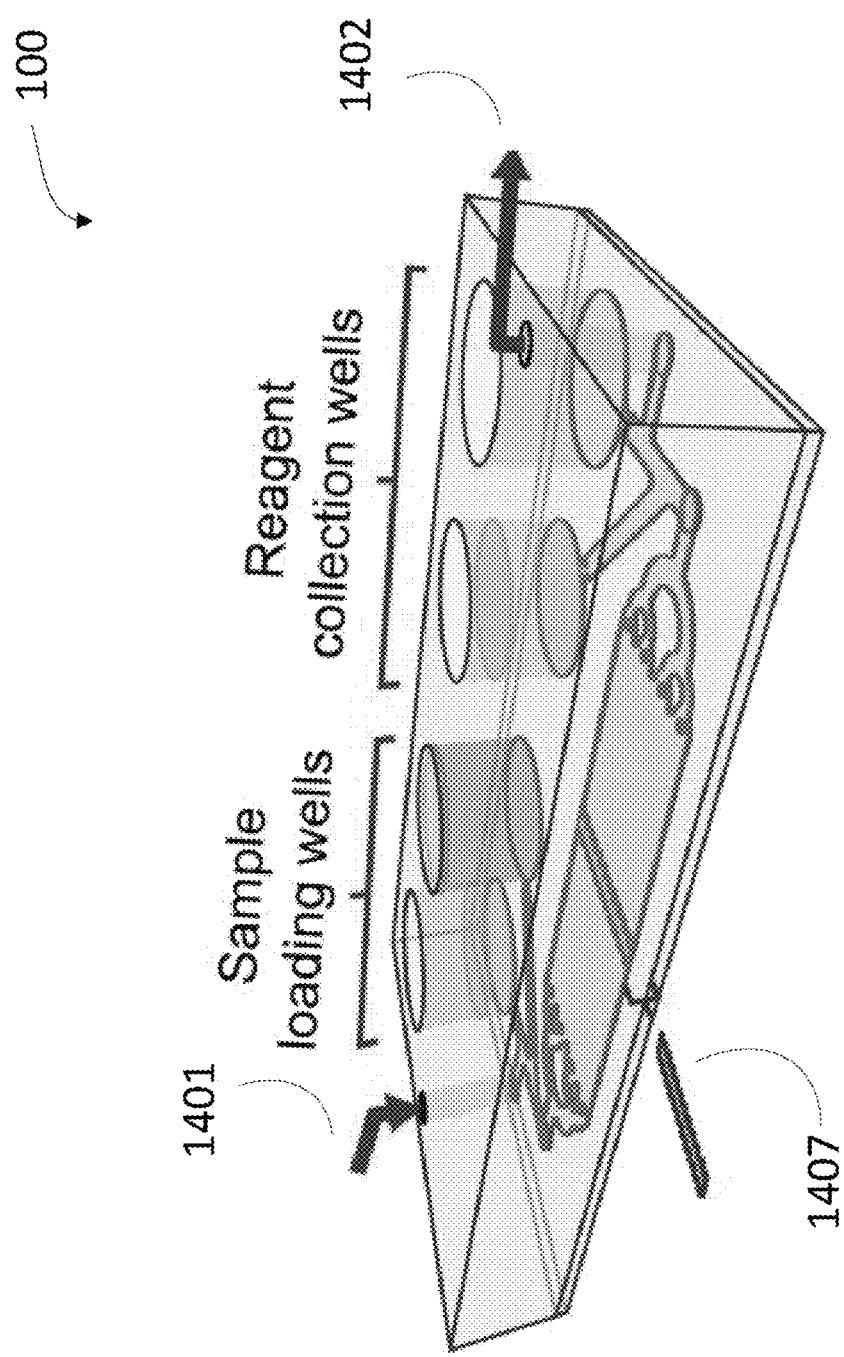
FIG. 14 is a schematic diagram of an acoustic chamber embodiment with polymer fluid routing layer coupled to a glass LSBAW channel. Sample loading/unloading/switching is achieved using pneumatic flow control and valves.

FIG. 14 is an embodiment of an acoustic separation device 100 including an inlet 1401, and outlet 1402, an enrichment structure 1407, and a plurality of wells configured to hold substances required for a reagent manipulation sequence. In the illustrated embodiment, a machined polymeric fluid routing layer is coupled to a LSBAW channel fabricated from an acoustically rigid material, e.g., glass, silicon, or metal. In other embodiments the LSBAW trap is embedded in a monolithic polymer cartridge.

During use of the acoustic separation device 100 illustrated in FIG. 14, a user may load reagents (e.g., antibodies, tracers, proteins, antibodies, RNA, DNA, carbohydrates, etc.) into sample loading wells (note only two are shown for simplicity). In some embodiments, sample cartridges are loaded into a stand-alone synthesizer and fluid loading/unloading/switching are performed automatically. Caps may seal each cartridge inlet/outlet, and a pneumatic flow controller (for example a MFCS™-EZ system) may pump/withdraw sample and buffer flow streams in sequence to complete a desired synthesis. Buffer switching (e.g., between HGS suspension, PBS, DI water, basic and acidic solutions) may be performed off-chip using a multichannel switch. Because sample in the channels is separated from the ultrasound actuator, no additional acoustic coupling/isolation layers are required. In some embodiments, the separation device 100 illustrated in FIG. 14 may be disposable.

LSBAW may be actuated using an off-the-shelf electronic drive (e.g., 33522A (Agilent Inc.) and 2100L (ENI Inc)). Electronic (ultrasonic) actuation, as well as fluidic control and routing, may be automated using LabVIEW and vendor-supplied control software. LabVIEW also enables real-time monitoring of electronic performance and fluorescence intensity in the LSBAW trap during system operation, yielding an effectively hands-free system after reagent loading. Automation may incorporate a graphical user interface (GUI) and push-button control.

Particle trapping capacity may be increased using a combination of three methods: i) increasing the lateral dimensions, ii) including additional enrichment structures, iii) stacking acoustic separation devices. Increasing the lateral dimensions (channel width w and etch depth h) is most straightforward; however, the depth must remain smaller than one-fifth the halfwavelength of the acoustic field (<~300 μm) to minimize vertical confinement of trapped particles.

Figure 15A:
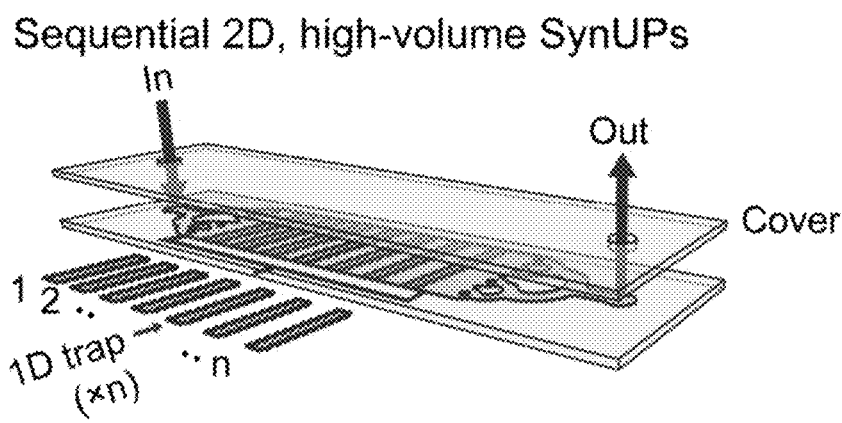
FIG. 15A depicts a high-volume sequential repetition of a 1D LSBAW trap.
Figure 15B:
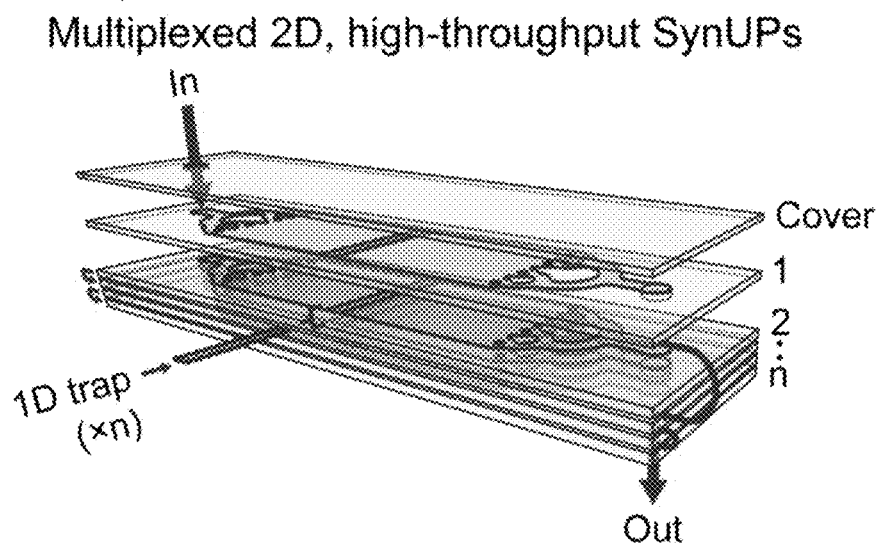
FIG. 15B depicts a multiplexed 1D LSBAW trap.
Figure 15C:
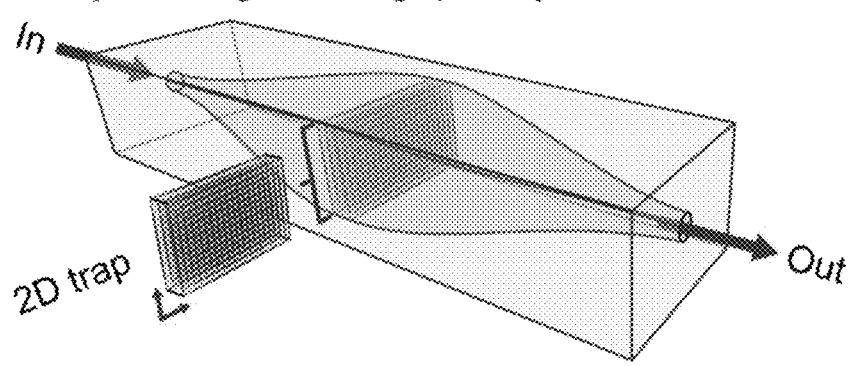
FIG. 15C depicts a 3D LSBAW trap.

As illustrated in FIG. 15A, additional trapping zones may be added to an existing single channel design to yield a sequential 2D, high-volume acoustic separation devices. In the embodiment illustrated in FIG. 15A, a plurality of pillar pairs occupy a common plane, wherein the common plane is parallel to the channel. Pillar arrays may be spaced such that all enrichment structures augment the pressure field at the same frequency. LSBAW chips may be stacked to form a multiplexed 2D, high-throughput acoustic separation device. As shown in FIG. 15B, individual trapping layers in this approach can be designed for sequential or parallel filling. In the illustrated embodiment, the outlet a acoustic separation device is coupled to an inlet of a subsequent acoustic separation device. Layers may be assembled using multi-step fusion bonding. FIG. 15C illustrates a high-throughput fully 3D LSBAW trap. In the embodiment illustrated in FIG. 15C, a plurality of pillar pairs occupy a common plane, wherein the common plane is perpendicular to the channel. Each scaling approach described above provides an increase in trapping capacity yielding a production rate in excess of the target 0.1 mg per run. In some aspects the trapping capacity yields a production rate in excess of the target 0.1 mg per run, 0.25 mg per run, 0.50 mg per run, 0.75 mg per run, 1.0 mg per run, or 1.5 mg per run.

EXAMPLES

The following examples illustrate various aspects of the disclosure and are not intended to be limiting in any manner.

Example 1

Separation of heterogeneous particle mixtures was demonstrated using suspensions of polystyrene beads (5 μm and 20 μm diameter at $5×10^5$ and $2×10^6$ per ml DI water, respectively; density 1.06 g $cm^{-3}$; Phosphorex) and hollow glass spheres (10 μm nominal diameter; Dantec Dynamics) decorated with fluorescent polyclonal secondary antibodies (rabbit anti-goat IgG Alexa Fluor 488; Abcam).

Figures 16A, 16B, 16C:
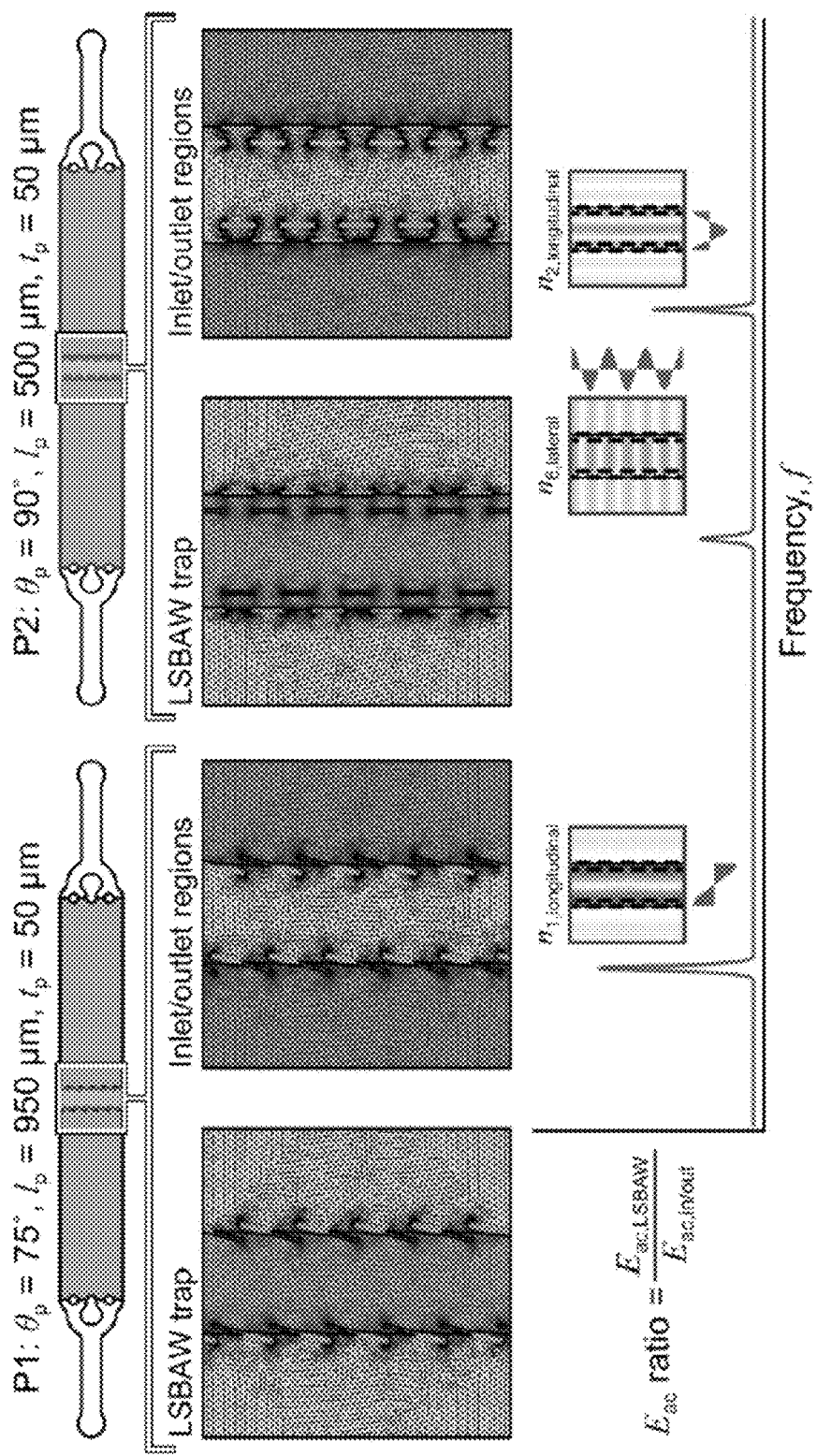
FIG. 16A depicts modeling domains highlighting the LSBAW enrichment (green) and inlet/outlet (blue) regions for channels with slanted pillar geometries.
FIG. 16B depicts modeling domains highlighting the LSBAW enrichment (green) and inlet/outlet (blue) regions for channels with lamellar pillar geometries.
FIG. 16C depicts LSBAW resonance identification using the ratio of acoustic energy density in the LSBAW trap to that in the inlet/outlet regions.
Figures 17A, 17B:
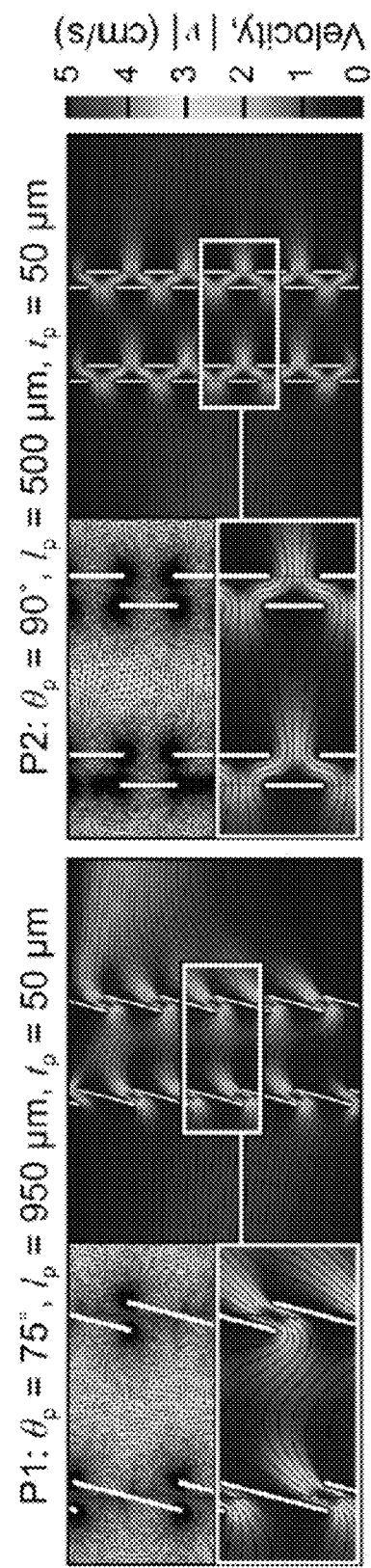
FIG. 17A depicts computational modeling of fluid flow through the enrichment region. Velocity contours and streamlines are shown for channels with slanted geometries.
FIG. 17B depicts computational modeling of fluid flow through the enrichment region. Velocity contours and streamlines are shown for channels with lamellar geometries.

The acoustics module of COMSOL Multiphysics was used to predict eigenfrequencies and eigenmodes for 2D representations of LSBAW separation channels (FIGS. 16A-C). The COMSOL Multiphysics microfluidics module was used to perform a laminar flow study on the same domain with a refined mesh (FIGS. 17A-B). Enrichment structures comprising parallel arrays of slanted (P1, angle of inclination to the flow, $\theta_p=75°$) and lamellar (P2, $\theta_p=90°$) pillars were designed to support a single node at approximately 500 kHz [gap width, $L_x=1.25$-$1.5$ mm, see FIGS. 13B, 13C, 16A, and 16B]. In both P1 and P2 cases studied, pillars were offset to eliminate direct longitudinal flow paths through the LSBAW trapping region; however, flow disturbances did not produce deviations from laminar behavior even for a relatively high flow rate of 100 µl min$^{-1}$ (Re~10, see FIGS. 17A and B). Acoustic analyses considered only the fluid (water; density $\rho=998$ kg m$^{-3}$; and speed of sound c=1481 m s$^{-1}$), and a dense mesh with triangular elements (minimum size 0.01 mm and maximum 0.1 mm) was applied to the fluid domain [see FIGS. 16A, and 16B for representative meshes]. Solid-liquid interfaces (i.e., the glass channel and pillar walls) were modeled using the sound hard boundary condition.

Enrichment performance was evaluated using suspensions of polystyrene (PS) beads (5 µm and 20-µm diameter at $2\times10^6$ and $5\times10^5$ beads per mL DI water, respectively; $\Phi_{ps}=0.165$; Phosphorex) and hollow glass spheres (10-µm nominal diameter, Dantec Dynamics) decorated with fluorescent polyclonal secondary antibodies (rabbit anti-goat IgG Alexa Fluor 488, Abcam), which were synthesized by following a protocol known to one of ordinary skill in the art. Inlet/outlet compression ports were used for static loading of particle suspensions. LSBAW chip assemblies were placed in a custom stage insert of an inverted microscope (Axio Observer z.1, Zeiss) for observation of acoustic particle migration. Enrichment frequencies were identified by sweeping transducer actuation over a 50-kHz range about predicted resonances of interest (33522A, Agilent; 2100L, ENI). When actuated at an experimentally determined longitudinal resonant frequency, particles were focused to nodal locations of the standing pressure field.

As shown in FIGS. 18 A-H, LSBAW experiments using polymer bead mixtures and antibody-decorated glass spheres confirmed predicted focusing/enrichment behavior. Enrichment capability was evaluated for four model cases: (i) 4.7-mm wide channel, slanted P1 pillar geometry, $f_1=0.579$ MHz, predicted $E_{ac}$ ratio~12; (ii) 10 mm channel, P1 geometry, $f_1=0.570$ MHz, $E_{ac}$ ratio~7; (iii) 4.7 mm channel, lamellar P2 geometry, $f_1=0.584$ MHz, $E_{ac}$~3; and (iv) 4.7 mm channel, P2 geometry, $f_4=2.47$ MHz, $E_{ac}$ ratio~33. The 20 µm PS and glass beads collected along the enrichment structure midline for both pillar geometries driven at the first longitudinal resonant mode [FIGS. 18B-D and 18F]. As predicted, particle focusing was roughly the same in 4.7 and 10 mm channels. Rapid agglomeration of particles was also observed to nodal locations of the field for the lamellar pillar geometry driven at 2.45 MHz [predicted fourth longitudinal resonance, FIGS. 18G and 18H]. Due to their positive acoustic contrast factors, both particles focused to the zero-pressure nodes of the field. The smaller-sized 5 µm PS beads were unaffected by the acoustic field.

Modal analyses provided only a qualitative description of the trapping potential of a given LSBAW architecture because several potentially significant effects, including the influence of the actuator/resonator, were neglected. In addition, the inherently 3D isotropically etched pillar features were represented in only two dimensions, which can cause device resonances to deviate from predicted higher harmonics of the fundamental frequency. In this context, predicted mode shapes display a remarkable similarity to observed terminal particle distributions of PS and fluorescent glass beads. Experimentally determined resonances were nearly identical to model predications (within 20 kHz). These results prove the potential for field amplification by the "pseudo walls" of an LSBAW trap to preferentially immobilize~10 µm particles from fluid media and other objects of subcritical diameter.

Example 2

Acoustic microfluidics enables non-contact separation and trapping of cell-sized objects, minimizing undesirable surface interactions and physical stress on sensitive biological samples. As illustrated in FIGS. 19A-B, particles suspended in a liquid are driven to pressure minima (nodes)/maxima (antinodes) when subjected to a standing acoustic field. The acoustic radiation forces responsible for this phenomenon arise due to an acoustic impedance mismatch between particles and suspension media. In addition to field properties (amplitude and frequency), these forces are influenced by particle geometric parameters (volume and shape) and a material-dependent acoustic contrast. Longitudinal acoustic trapping employs a standing ultrasonic wave in parallel with the flow channel yielding multiple nodal locations along the direction of flow. In the vicinity of these pressure minima, acoustic radiation forces (Fac) oppose viscous drag (Fd) to preferentially focus and confine particles that exceed a threshold size (e.g., trapping microcarriers and not antibodies in solution). Use of ultrasound in the 1-10 s of MHz range limits manipulation to particles on the order of 1 µm and larger, excluding nanoscale antibody constructs; however, use of micron-scale particles (microcarriers) to enable separation and control over nanometer-scale objects (antibodies and tracer molecules) has been demonstrated. LSBAW extends the longitudinal trapping concept to incorporate pairs of perforated 'pseudo walls' oriented perpendicular to the inflow direction, locally augmenting the acoustic pressure field. Thus, particles of supracritical diameter are confined to a single location along the channel. Preliminary studies prove that LSBAW architectures and flow parameters can be tuned to enable nanomaterial synthesis on ultrasound-confined particles (Syn-UPs) in an automated and scalable format.

Figure 19:
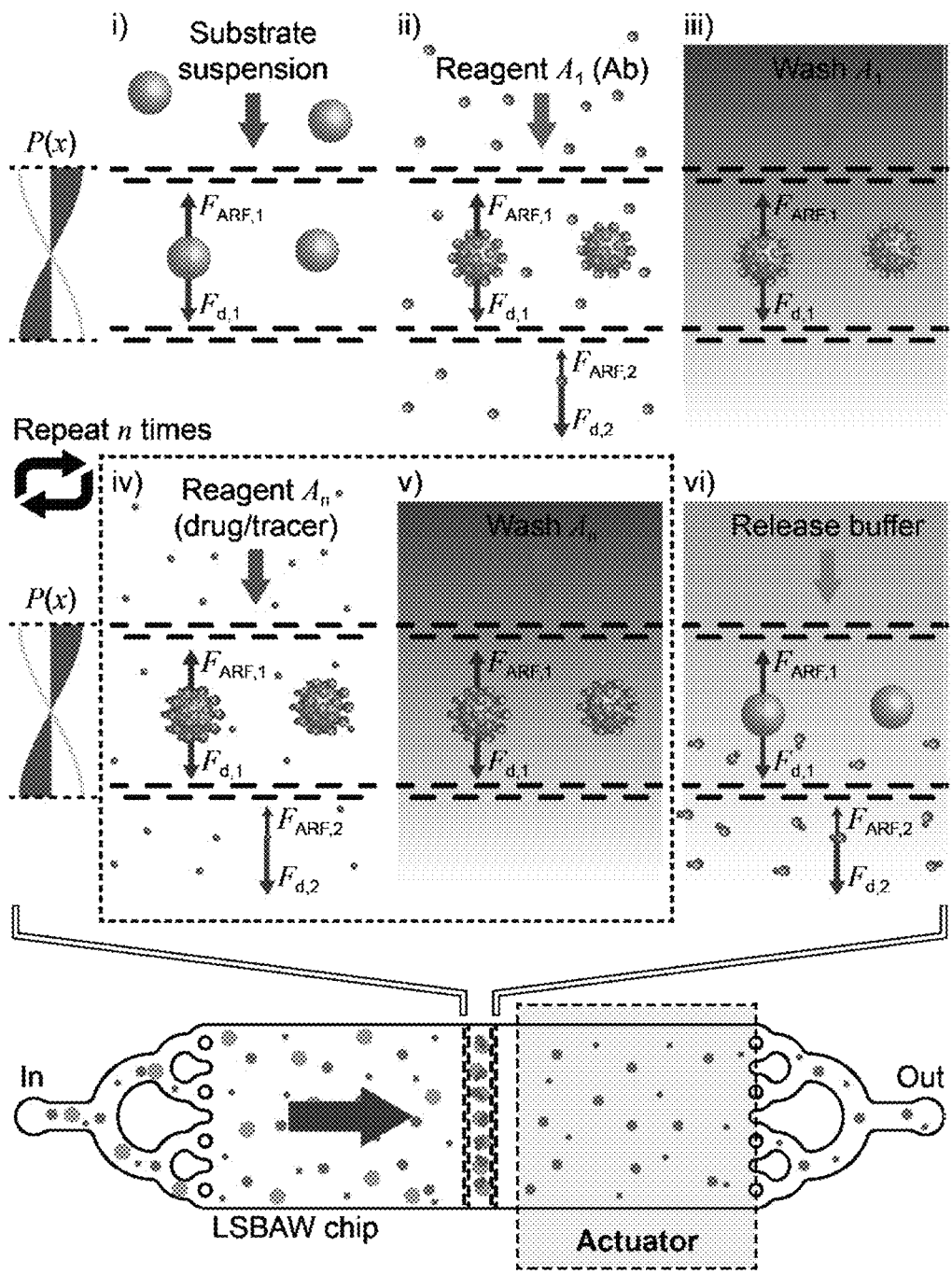
FIG. 19 depicts an example process for LSBAW-mediated synthesis using a microdevice which generates a pressure field conducive to trapping of positive acoustic contrast particles, which migrate toward regions of low pressure within a pillar structure. The process includes the steps of (i) acoustically focusing Protein G-coated microparticle substrates to the pressure node of an LSBAW pillar array; (ii) introducing Reagent $A_1$ (antibody solution), causing Protein G to bind specifically to the $F_c$ portion of the antibodies and immobilizing them on the ultrasound-confined substrates; (iii) washing remaining antibodies (which are unaffected by the acoustic field) with a buffer solution; (iv) and (v) modifying bound antibodies through sequential introduction and washing of additional reagents $A_n$; (vi) detaching antibodies from microparticle substrates using a release buffer and collecting the detached antibodies at the outlet.

In the example embodiment shown in FIG. 19, protein G-terminated HGS is focused from a heterogeneous solution to an acoustic pressure node, where they remain stationary during reagent flow and subsequent processing steps. Introduced antibodies specifically bind to the open Protein G groups on the surface of the HGS, creating activated HGS-antibody (aHGS-Ab) complexes. After incubation, excess antibody is removed and recycled from the system. A release buffer (low pH solution) is used to detach antibodies from the HGS to allow for collection from the microchannel. In the example embodiment shown in FIG. 19, the cycle of adding reagents and washing the trapped particles can be repeated n times, where n can be any number of cycles required to complete the desired reaction. For example, n may be any integer from 1-20.

Figure 20:
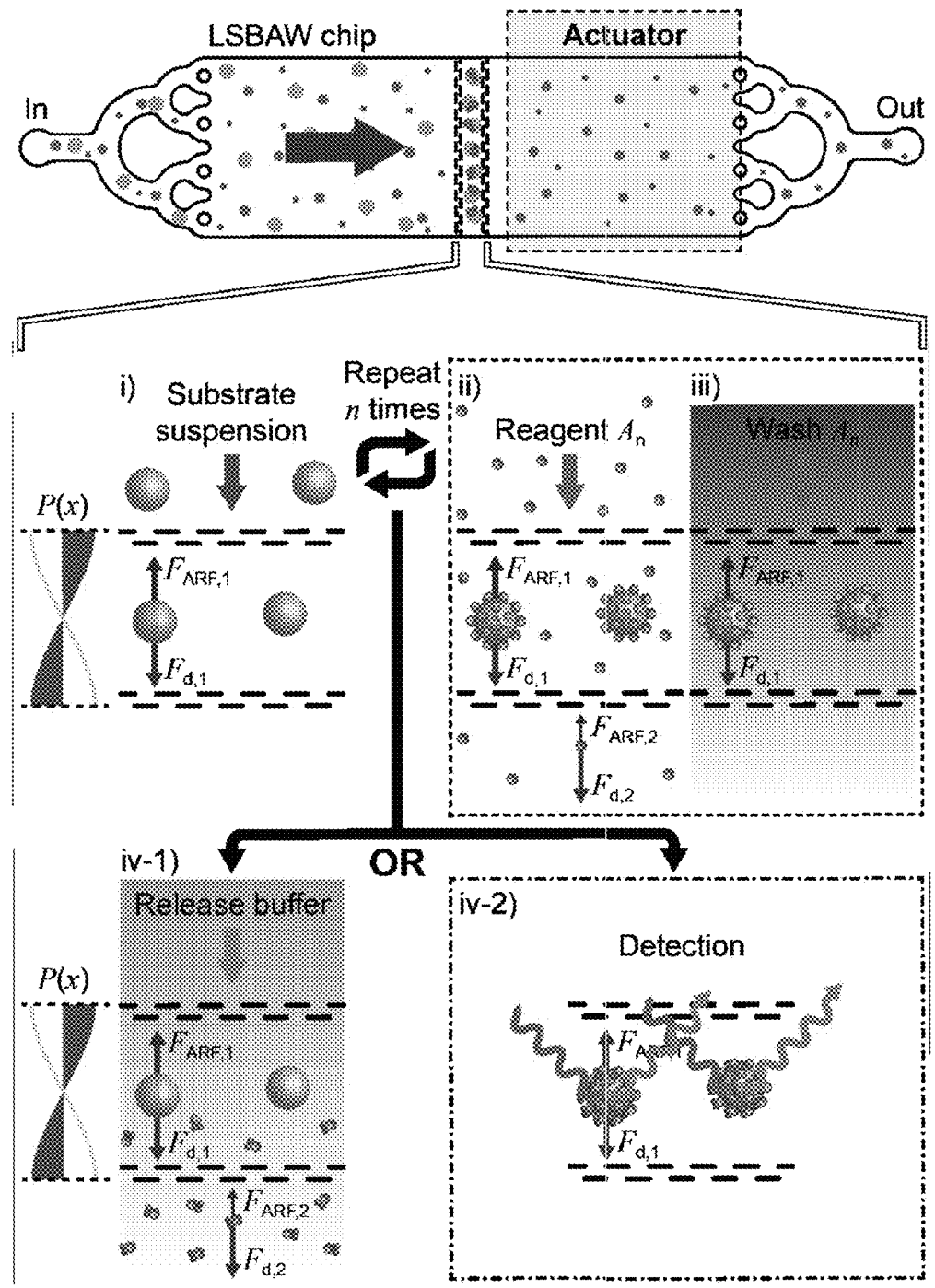
FIG. 20 an example process for LSBAW-mediated synthesis and detection using a microdevice in which is generated a pressure field conducive to trapping of positive acoustic contrast particles, which migrate toward regions of low pressure within a pillar structure. The process includes the steps of (i) acoustically focusing Protein G-coated microparticle substrates to the pressure node of an LSBAW pillar array; (ii) introducing Reagent $A_1$ (antibody solution), causing Protein G to bind specifically to the $F_c$ portion of the antibodies and immobilizing them on the ultrasound-confined substrates; (iii) washing remaining antibodies (which are unaffected by the acoustic field) with a buffer solution; and (iv-1) modifying and releasing bound antibodies through sequential introduction and washing of additional reagents $A_n$; or (iv-2) detecting the bound antibodies while they remain in the LSBAW microdevice.

FIG. 20 demonstrates the use of the LSBAW platform for antigen detection. In the example embodiment, an LSBAW microfluidics device generates a pressure field conducive to trapping of positive acoustic contrast particles, which migrate toward regions of low pressure within the pillar structure (FIG. 20). In FIG. 20, steps ii and iii represent serial chemical introduction and wash steps performed in a well-controlled manner for the development of ordered self-assembled monolayers (SAMs). Depending on the application, resultant monolayers can be: (iv-1, FIG. 20)

cleaved using a release buffer and collected at the outlet, or (iv-2, FIG. 20) continuously monitored and assessed within the channel using known detection methods, for example fluorescence microscopy.

Figures 21A, 21B, 21C, 21D, 21E, 21F, 21G:
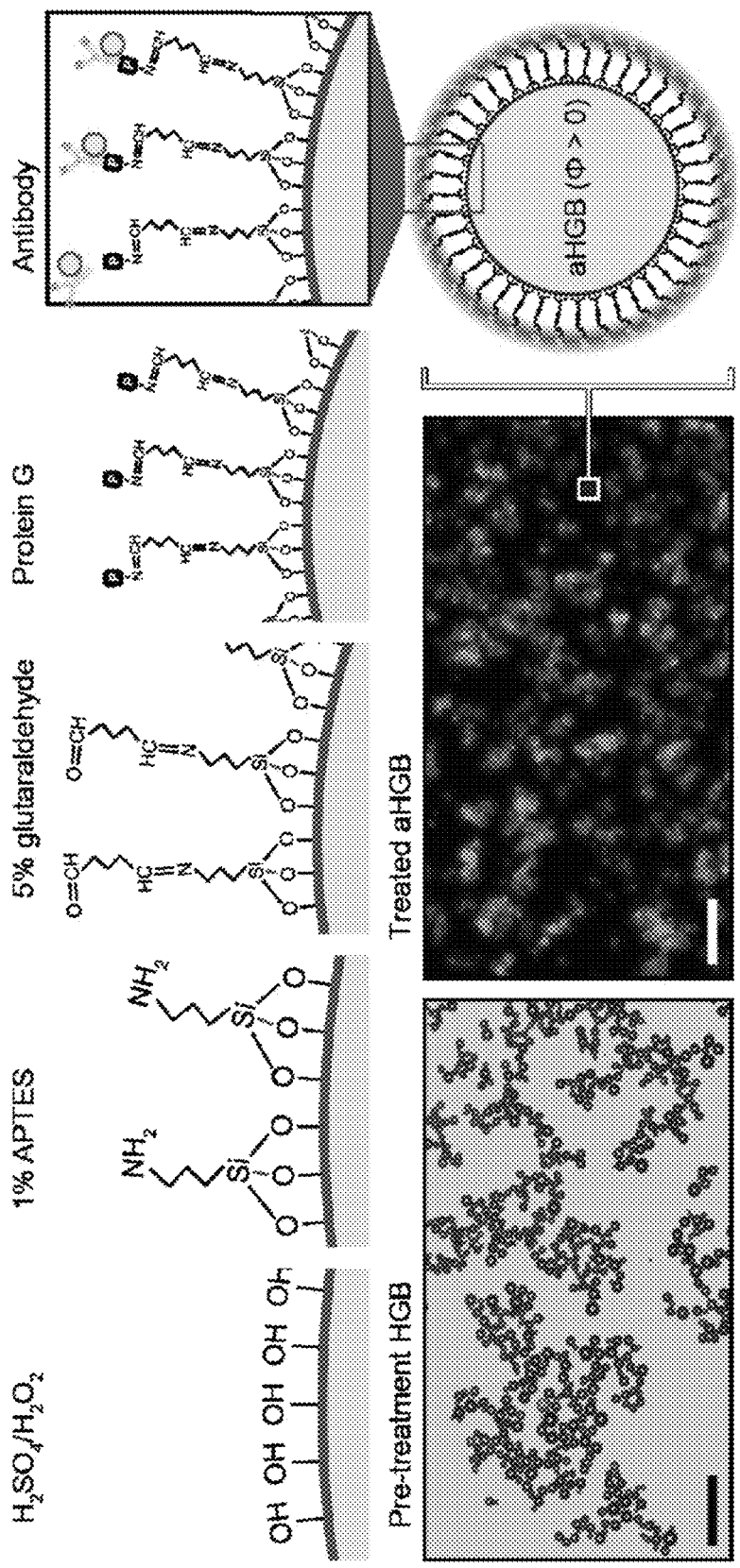
FIG. 21A illustrates a first incubation step of hollow glass sphere functionalization and labeling.
FIG. 21B illustrates a silanization step of hollow glass sphere functionalization and labeling.
FIG. 21C illustrates a APTES activation step of hollow glass sphere functionalization and labeling.
FIG. 21D illustrates coupling of Protein G to the activated surface of a hollow glass sphere.
FIG. 21E illustrates a second incubation of the antibody step of hollow glass sphere functionalization and labeling. In some aspects, the second incubation step is performed within the acoustic separation device.
FIG. 21F is an image of a pre-treated hollow glass sphere.
FIG. 21G is an image of a treated hollow glass sphere.

To demonstrate the suitability of its surface chemistry with respect to microcarrier-based AC assembly, borosilicate HGSs (HGS-10, Dantec Dynamics A/S) with a mean diameter of 10 μm±3.5 μm were functionalized as shown in FIGS. 21A-G. FIG. 21A illustrates incubation of HGS in a mixture of $H_2SO_4$ (98%) and $H_2O_2$ (aq., 30%) 3:1 (vol.) for 2 hrs to produce open surface hydroxyl groups. FIG. 21B illustrates silanization of hydroxyl groups using 1% (v/v) 3-aminopropyltriethoxysilane (APTES, Sigma-Aldrich Inc.) in anhydrous ethanol for 10 minutes under constant agitation. FIG. 21C illustrates APTES evaporation at 100° C. for 1 hr, and activation of APTES with 5% (v/v) glutaraldehyde in phosphate buffered saline solution (1×PBS) for 3 hrs. FIG. 21D illustrates incubation in a solution of recombinant Protein G from G. Streptococci (1 mg/mL in PBS) at 4° C. for 3 hrs to establish specificity to antibodies. FIG. 21E illustrates protein G-terminated HGS incubating with fluorescent antibody (5 μg/mL in PBS; rabbit anti-goat IgG Alexa Fluor 488, Abcam Inc.) for 1 hr at 4° C. FIG. F is a bright-field microscopy image of pre-treated HGSs and FIG. 21G is a fluorescence microscopy image of treated HGS verifying the reaction chemistry. The validated protocol may be adapted slightly for in-channel synthesis by reducing incubation times to reflect room temperature conjugation of antibodies to acoustically-confined HGS. Conversely, in-channel SynUPs can be performed using a temperature-controlled chip.

To provide a wide range of material properties, different classes of microcarriers may be used with the present acoustofluidic particle manipulation system including: i) solid silica microspheres, ii) porous silica microspheres, iii) solid polymeric microspheres, iv) hollow polymeric microspheres, v) solid elastomeric microspheres, and vi) hollow elastomeric microspheres. For reference, the specific surface area available for synthesis and antibody conjugation (defined as surface area per particle mass) of HGS is estimated to be 1 $m^2$/g. Solid silica spheres are available commercially in a range of diameters (from sub-1 to 10 s of μm). Silica contains no sodium, boron, and aluminum impurities leading to an order of magnitude increase (versus the borosilicate HGS) in open surface amine density after hydroxyl addition and APTES treatment (see FIG. 21A,B). Thus, absence of these impurities increases the number of available binding locations for the Protein G-terminated self-assembled monolayer (SAM) for antibody binding (FIG. 21D). This increase in binding location density is offset by an increase in particle density yielding a specific surface area of 0.6 $m^2$/g; however, the increased density also enhances acoustic contrast between particles and media, producing larger trapping forces and improving trapping capacity. Increased density allows for adequate trapping forces on smaller particles such as 5 μm size which further extends the bead trapping capacity of a given acoustic trap. Finally, solid silica spheres exhibit increased stability over hollow counterparts as they are less prone to bead fracture during handling and manipulation in the acoustic field.

Specific surface area is increased by decreasing the particle density or through addition of surface roughness and porosity (and thus surface area). Higher density is preferred for acoustic focusing and confinement. Commercially available porous silica microspheres are available in a range of pore sizes from 100 to 500 Å with optimized pore volume and special functional groups to support surface reactions. Relative to solid silica particles and HGS, porous microspheres exhibit a more than two orders of magnitude increase in specific surface area (~250 $m^2$/g) for the same 5 μm particle diameter. Stability should be similar to that of solid silica particles.

Figure 22A:
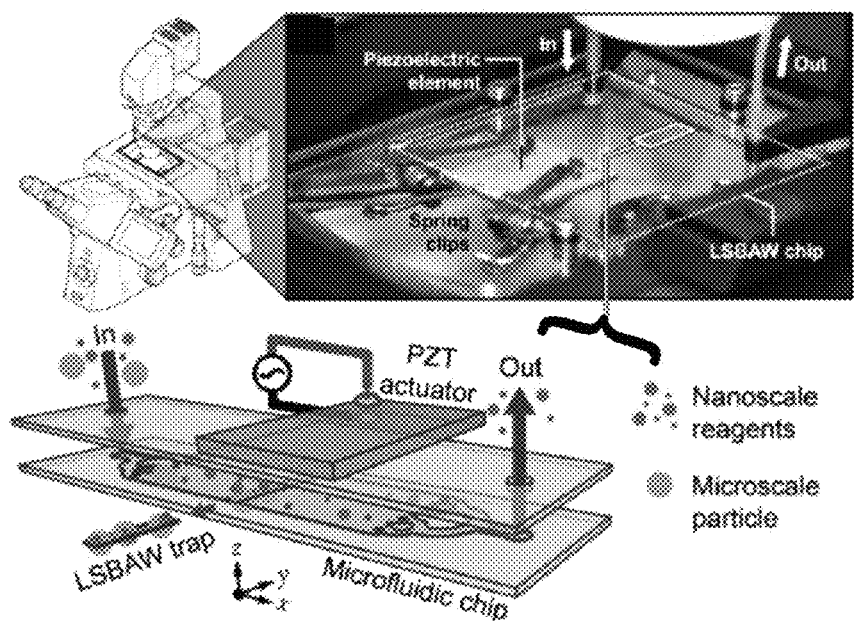
FIG. 22A depicts a realized device assembly of an acoustic chamber implementation.
Figure 22B:
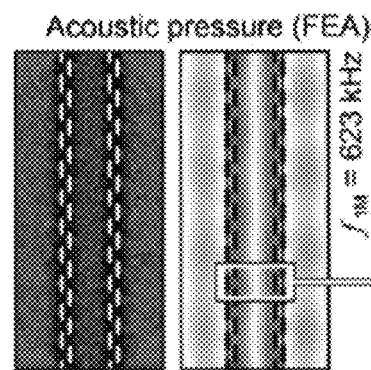
FIG. 22B depicts a computational model-predicted pressure field within a lamellar pillar geometry under actuation.
Figure 22C:
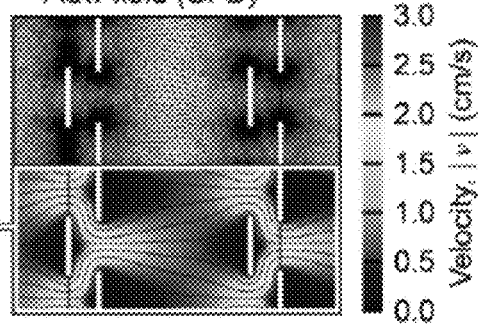
FIG. 22C depicts computational modeling of fluid flow through the enrichment region. Velocity contours and streamlines are shown for channels with lamellar geometries.

FIG. 22A depicts the experimental setup for actuation of the LSBAW channel using a clamped 1.5-mm thick PZT-8 piezoelectric transducer (P880, American Piezo Ceramics Inc.) to generate the standing acoustic field within the device. Contact between the actuator and the glass channel was maintained using an ultrasound gel (McKesson Corp.) to provide good acoustic coupling. A syringe pump (Legato 110, KD Scientific Inc.) introduced reagents and controlled their flow rate through the device. Inlet/outlet tubing was held in place using microfluidic probes (CorSolutions LLC). An inverted microscope (Axio Observer z.1, Carl Zeiss AG) allowed for visual observation of the LSBAW trapping region throughout the synthesis. The piezoelectric transducer was driven using an amplified AC signal (33522A, Agilent Technologies Inc.; 2100L, Electronic Navigation Industries) at frequencies predicted by the COMSOL computational model, as shown in FIG. 22B. The drive waveform was first set to a nominal operating frequency corresponding to the highest average pressure field magnitude within the acoustic trap relative to the inlet/outlet regions. These resonances should exhibit the highest amplification, greatest stability, and desired directionality (i.e., orthogonality to the inflow direction). The actual first half-wavelength resonance was found by scanning around this nominal (predicted) operating frequency in increments of 5 kHz.

Figure 22D:
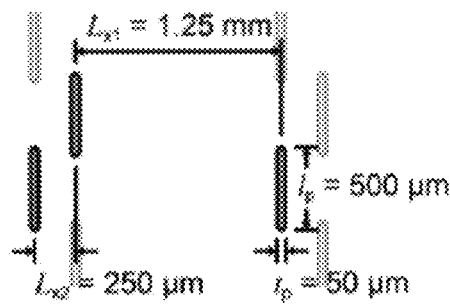
FIG. 22D depicts a lamellar pillar geometry and microscope images and schematics of glass LSBAW enrichment regions with lamellar pillar geometries.
Figure 22D:
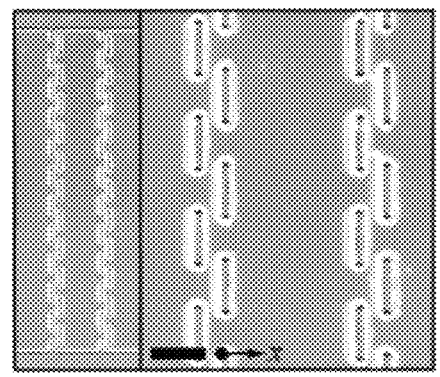

Perforated pseudo-walls incorporated into the channel (shown in FIG. 22D) locally augment the standing acoustic pressure field to balance drag forces on microcarriers during fluid flow. Thus, particles are preferentially focused at a prescribed location within the device. The orthogonal orientation of pressure nodes within the LSBAW trap contrasts that of prevailing acoustophoretic devices where nodes/antinodes are parallel to the inflow direction. Critical operational eigenfrequencies, which correspond to longitudinal half-wave resonances of the pillar array, exhibit a relative increase in acoustic energy density of the trap versus the channel inlet and outlet regions. Selected optimum operating frequencies are inherent to the geometry of the device and create robust synthesis conditions. Commercially available finite element analysis (FEA) software, COMSOL Multiphysics 5.2a with acoustics module, was used to model the harmonic response of the LSBAW channel and to identify the desired first half-wave resonance for effective particle trapping and synthesis.

The LSBAW microchannel was fabricated using standard isotropic wet etching of photolithographically-patterned 63.5 mm by 63.5 mm chrome-coated soda lime glass mask blanks (Telic Co.) in a solution of hydrofluoric acid (aq., 49%), nitric acid (aq., 69%) and deionized (DI) water in a ratio of 2:1:6 (vol.) to a final depth of 62 μm. The etched glass channel was sealed by a second 63.5 mm by 63.5 mm blank (Telic Co.) using a calcium-assisted bonding technique.

Figures 23A, 23B, 23C:
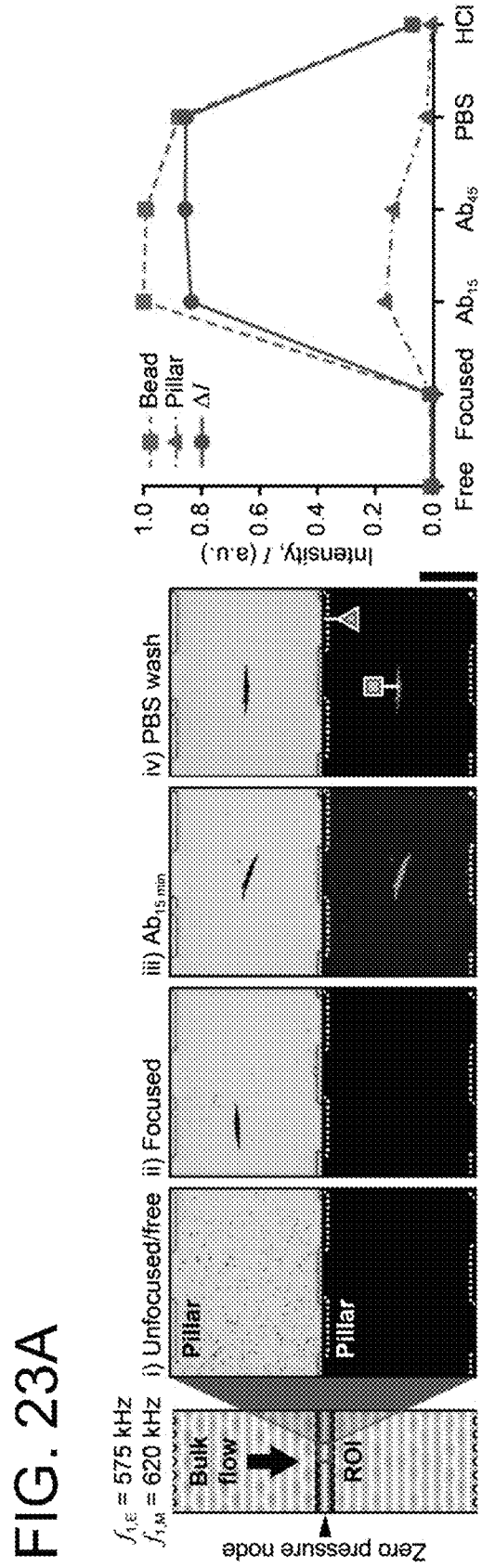
FIG. 23A depicts a computational model-predicted pressure field within a lamellar pillar geometry under actuation. A zero pressure node exists between two
FIG. 23B illustrates an LSBAW demonstration, including sample fluorescent images taken after incubation and removal of excess antibodies with regions of sampled intensity for the beads and pillars noted.
FIG. 23C depicts corrected intensity I (normalized to highest value) of a bead cluster, pillar, and ΔI taken at 6 points during a synthesis procedure.

A complete sequence of HGS focusing and confinement, antibody capture, purification, and release is shown in FIGS. 23A-C. When actuated by a 1.5 mm thick PZT-8 piezoelectric transducer, Protein G-terminated HGS were focused to a LSBAW midline at a predicted first half-wave resonant frequency of 570-590 kHz, as shown in FIGS. 23B(ii). Antibody solution was introduced over ultrasound-confined HGS at a flow rate of 7 μL/min for 10 min followed by prolonged incubation (total 45 min residence time) to ensure surface saturation (see FIG. 23B(iii) for labeling at 15 min). Excess antibody was removed using a phosphate buffered saline (1×PBS) wash at 7 μL/min for 10 min as shown in FIG. 23B(iv). Antibody detachment from HGS was achieved using a low pH wash of 2% HCl at 7 μL/min for 10 min.

Antibody to HGS binding was assessed by measuring the intensity of the beads and bead cluster relative to that of the pillar array. FIG. 23C is a plot of the corrected intensity I of the beads, pillar, and their difference ($\Delta I = I_{bead} - I_{pillar}$) at each of 7 different synthesis stages. Area of sampling was held constant between pillar and beads, as shown in FIG. 23C, and the final values were normalized to the highest intensity (the bead intensity after 15 minutes of antibody introduction). There was no intensity difference in the bead fluorescence prior to the introduction of antibodies. Surface saturation of the antibodies is achieved by the end of the 45-minute incubation in antibody solution. After introduction of the release buffer, $\Delta I$ falls from 0.86 a.u. to 0.07 a.u. The non-zero final bead intensity is likely due to remnant surface antibody that is blocked from removal by bead aggregation even after prolonged (30 min) exposure to the release buffer.

Figures 24A, 24B:
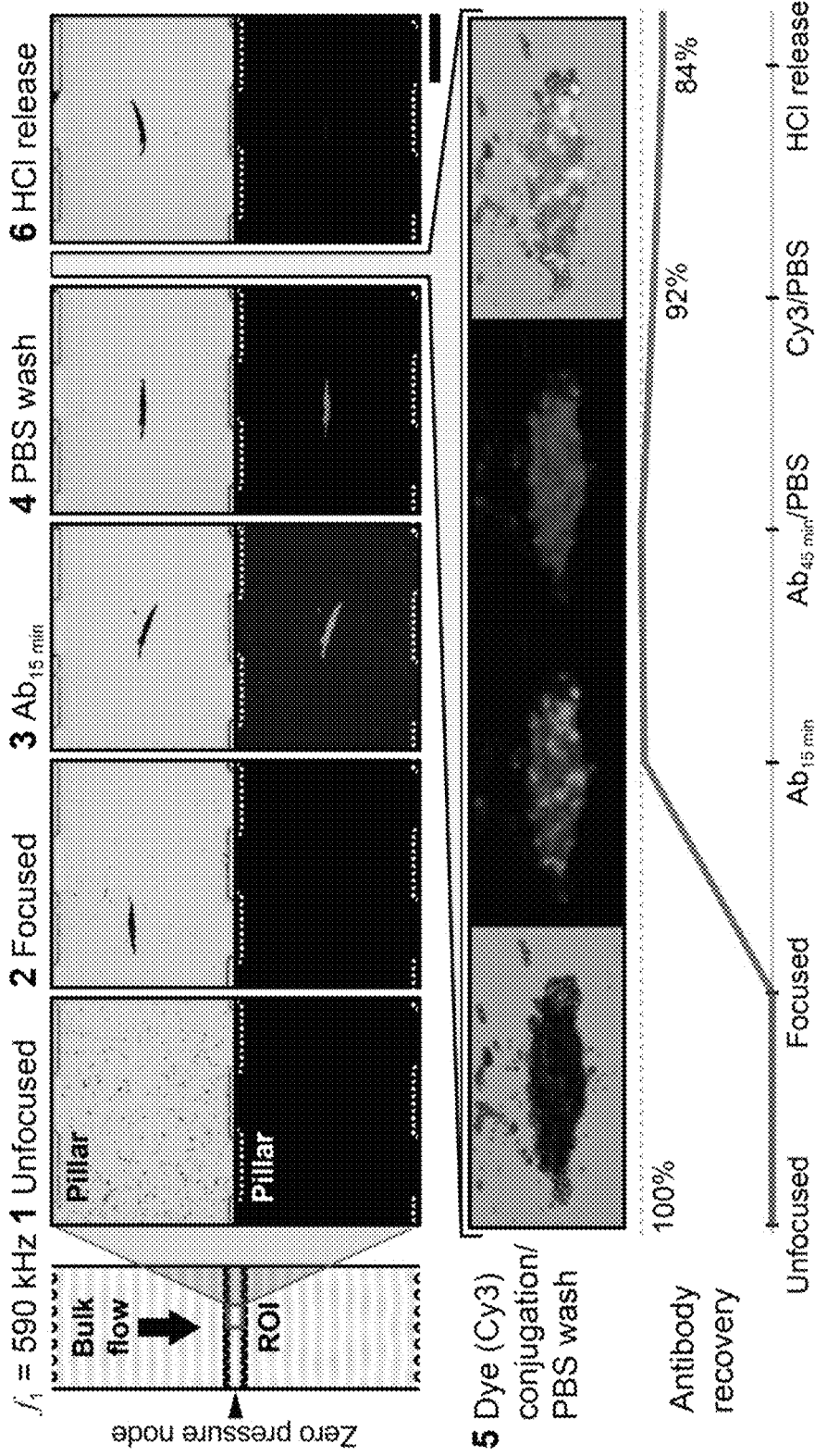
FIG. 24A depicts fluorescence microscopy images showing modification of labeled antibodies bound to ultrasound-confined hollow glass sphere capture particles.
FIG. 24B depicts antibody recovery a each step of a SynUPs demonstration.

To demonstrate modification of immobilized antibodies bound to HGS, fluorescent antibodies were captured on ultrasound-confined, protein G-terminated HGS as described above. Excess antibody was removed using a phosphate buffered saline (1×PBS) wash at 7 μL/min for 10 min. Antibody detachment from HGS was achieved using a low pH wash of 2% HCl at 7 μL/min for 10 min. A complete sequence of HGS focusing and confinement, antibody capture, purification, and release is shown in FIGS. 24A-C.

Figures 25A, 25B, 25C, 25D:
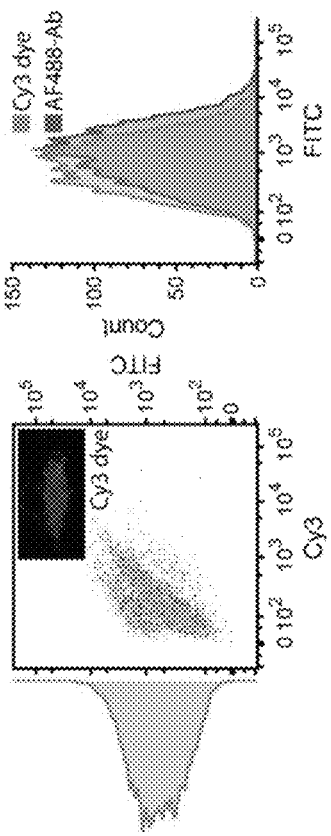
FIG. 25A depicts validation of a conjugation process by showing that bare beads show no fluorescence in FITC and Cy3 channels.
FIG. 25B depicts validation of a conjugation process by showing that Alexa488-labelled Ab attached to beads shows fluorescence in an FITC channel.
FIG. 25C depicts validation of a conjugation process by showing that additional labeling with Cy3 dye leads to fluorescence in both FITC and Cy3 channels.
FIG. 25D depicts validation of a conjugation process by showing that Alexa488-Ab and Alexa488-Cy3-Ab show very similar FITC channel distribution.

To demonstrate conjugation of immobilized antibodies bound to HGS, FITC labeled Ab was captured on ultrasound-confined, Protein G-terminated HGS as described above. Excess free antibody was removed and bound antibodies were labeled with an NHS ester dye (sulfo-cyanine3 NHS ester, Lumiprobe) under basic conditions (FIG. 24A, step 5). Fluorescence microscopy indicated good coverage of both the fluorescent antibody (green fluorescence) and NHS ester dye (red fluorescence). Validation of the conjugation process was also performed using flow cytometry of the beads as shown in FIGS. 25A-D. FIG. 25A shows that bare beads show no fluorescence in FITC and Cy3 channels. FIG. 25B shows Alexa488-labelled Ab attached to the beads shows fluorescence in FITC channel. FIG. 25C shows additional labeling with Cy3 dye leads to fluorescence in both FITC and Cy3 channels. FIG. 25D shows Alexa488-Ab and Alexa488-Cy3-Ab show very similar FITC channel distribution (92% overlap) demonstrating minimum leaching of the Ab during synthesis under SynUPs conditions. The flow cytometry data demonstrated minimum leaching of the Ab during synthesis under SynUPs conditions (with 92% of Abs remaining on the beads after wash-conjugation-wash cycle). Following modification, fluorescent antibodies were again detached from HGS using a low pH release buffer. The overall recovery yield was found to be 84%, as shown in FIG. 24B.

Figure 26:
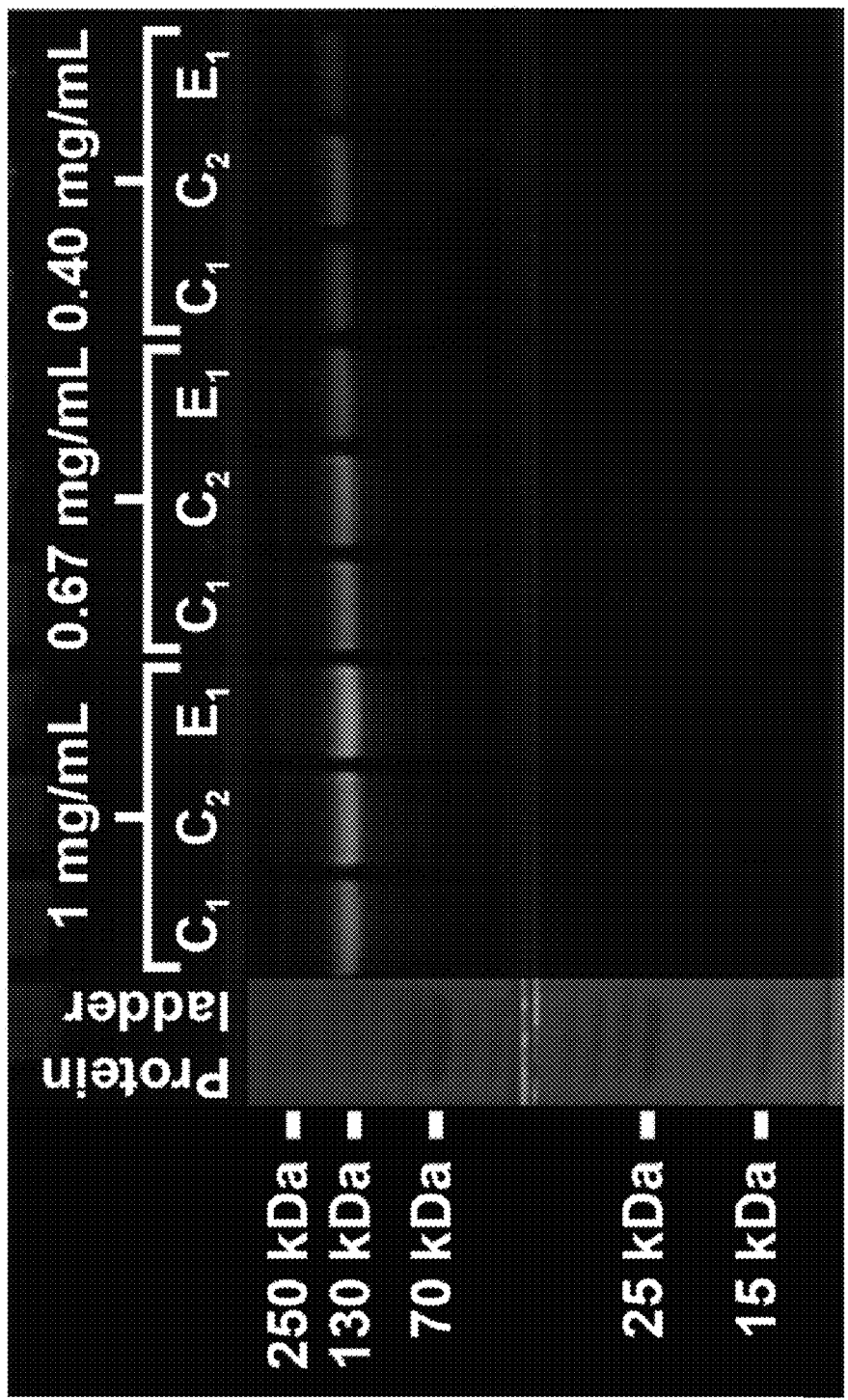
FIG. 26 depicts a gel electrophoresis showing stability of an antibody after a conjugation process.

The stability of the AC synthesized using SynUPs was confirmed with gel electrophoresis, as shown in FIG. 26. The mass of the antibody was judged by the molecular weight with no observed fragments in the gel.

Example 3

Conjugation often adversely affects antibody specificity due to perturbations at the fragment antigen-binding, (Fab) domain. Lower specificity decreases therapeutic and diagnostic potential while increasing toxicity and side effects. The most common targets for modifying Ab molecules are primary amine groups that are present as lysine side chains. These groups are easily modified due to their steric accessibility and high reactivity. However, lysines are distributed throughout the antibody (including Fab regions) limiting the applicability of this conjugation method. A traditional alternative to primary amine modification is to conjugate through sulfhydryl groups. However, since antibodies do not have free sulfhydryl groups available, antibodies require reduction of the cysteine bonds to access them. If not carefully controlled, reduction results in decreased molecular stability of an antibody lowering specific binding. To date, there are two clinically approved ADCs, Adcetris and Kadcyla, which are stochastically conjugated through lysine or cysteine residues. Both methods may implemented in SynUPs using NHS-lysine chemistry.

The major objective in site-specific ADC/ATC synthesis is to produce the conjugate with a specificity similar to the parent antibody. Ideally, that is achieved through a tightly controlled site-specific conjugation only at the Fc domain of the antibody to preserve the sensitivity of the Fab parts.

Figure 27:
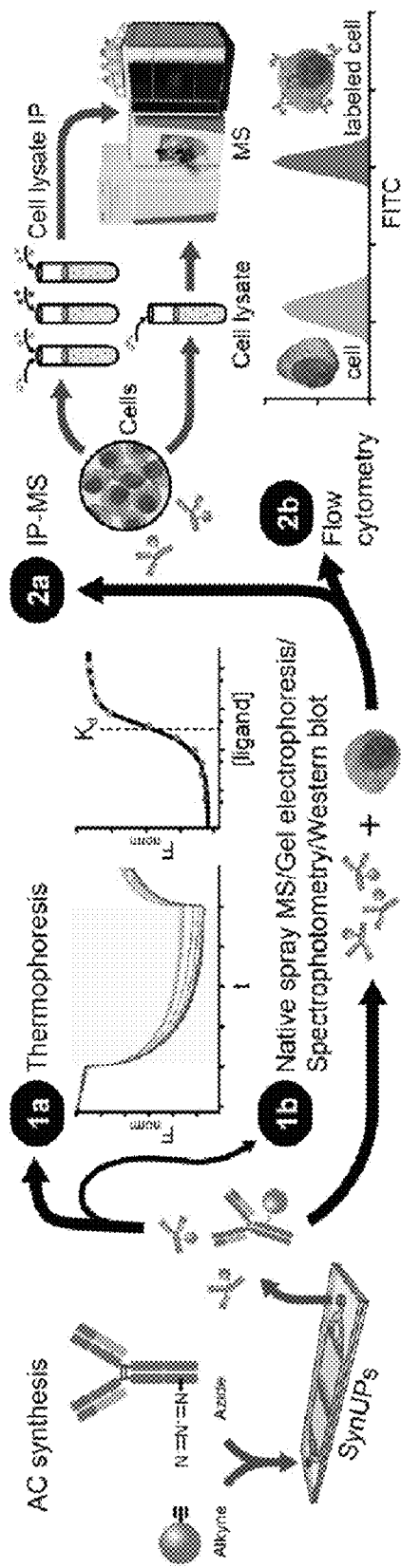
FIG. 27 depicts a synthesis and evaluation of antibody specificity.
Figures 28A, 28B:
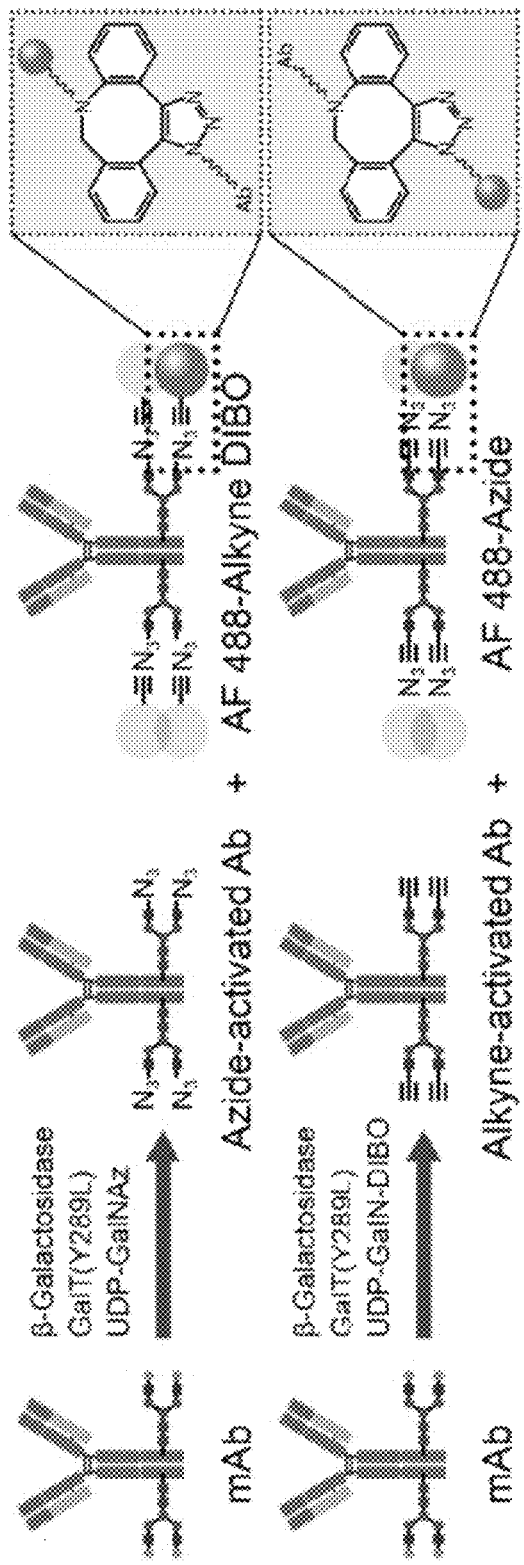
FIG. 28A depicts an antibody-azide formation process.
FIG. 28B depicts an antibody-alkyne formation process.

Schematics of the synthesis are shown in FIG. 27. Two complementary strategies may be implemented (shown FIGS. 28A-B). IgGs contain two conserved glycosylation sites in their heavy chains. We will use these sites to introduce an azide as shown in FIG. 28A or an alkyne FIG. 28B for subsequent clicktype conjugation. Ab-azide and Ab-alkyne forms of generic IgG antibodies will be prepared in solution using SiteClick kits (ThermoFisher) according to manufacturer recommendations and published procedures. After modification, a typical activated Ab (e.g., Ab-azide) contains up to four activated sites for binding with modified fluorophore-alkynes. The counterpart Alexa-488-alkyne DIBO or Alexa-488-azide are commercially available, for example from ThermoFisher.

Synthesis of the conjugates via non-copper click chemistry may be performed using SynUPs similar to the process described in FIGS. 19A-B. Due to spatial constraints on the microparticle, two sites are expected to be available for reactions making the conjugation site-specific and the product homogeneous.

The stoichiometry of ACs may be assessed by spectrophotometry, intact mass measurement and native spray MS using a Thermo Exactive EMR. Strategies with sufficient purity (>90 area %) may be selected for the next sub-aim.

To be useful for therapeutic or diagnostic development, the conjugation strategy must yield an AC with comparable or higher binding affinity and specificity for the target antigen as the parent antibody, which may be assessed as illustrated in FIG. 29. Instrument performance may be tested preparing an AC composed of anti EGFR mAb EP38Y and the fluorophore AlexaFluor 488 using the conjugation methods specified above (site-specific and stochastic, i.e., lysine).

For quantitative binding measurements, MicroScale Thermophoresis (MST) technology is used. This technique enables evaluation of Kd, however it requires purified antigens. Human EGFR protein is used for this purpose. In this approach the two proteins (the labeled Ab and antigen) are be mixed in different molar concentrations. The concentration of the labeled EP38Y is kept constant at ca. 5 nM while the concentration of the unlabeled binding partner is varied.

After incubation for 10 min at room temperature, the samples are loaded into hydrophilic glass capillaries and placed into a Monolith NT.115 pico (NanoTemper Technologies) to generate a binding curve and calculate the Kd similar to the data shown in FIG. 29. We expect to demonstrate similar or significantly better (lower) Kd using the site-specific conjugates.

Affinities of ACs and controls may be compared using flow cytometry on A431 squamous carcinoma cells with a high expression of EGFR, serially diluting the antibodies until a reduced shift is observed.

Product yield is directly related to the particle trapping capacity of the acoustic separation device structure. For the chemistry used, the surface density of antibodies on HGS is approximately $3 \times 10^{13}$ molecules per cm. For the current prototype SynUPs shown in FIGS. 12A-B, that uses 60 µm depth LSBAW geometry, a maximum trapping capacity of ~100,000 beads is estimated, which yields a potential product mass of ~1 µg per run. To reach a production rate of 100 µg per run, for example, available surface area (and bead count) must be increased. Typical microfluidic technologies rely on two-dimensional (2D) planar fabrication techniques adapted from established microelectronics industry processes. Parallelization of resulting planar microchannels is limited to one dimension (1D). In conventional acoustic microfluidics (i.e., with aqueous solutions, speed of sound c 1500 m/s, frequency of operation f=1-10 MHz), one or both lateral dimensions (h×w) are also fixed by the necessity to support a standing acoustic wave [w, h=c/(2 f)]. The disclosed LSBAW architectures overcome these limitations through innovative arrangement of the standing pressure field perpendicular to the inflow direction. Perforated 'pseudo walls' reflect acoustic waves while permitting sample flow.

This example discloses a novel method for synthesis of antibody constructs on microcarrier particles that are acoustically immobilized within a microfluidic channel. The perforated pseudo walls of the LSBAW channel provide local pressure field amplification to overcome the drag forces arising from reagent flow. After establishing appropriate surface chemistry for antibody binding to borosilicate beads, simple capture, purification and release of labelled antibodies were conducted to demonstrate in-channel synthesis. The LSBAW acoustic separation device also enables capture of free antibodies from solution and modification (e.g., additional labelling) prior to purification and detachment. While the current method is limited to a small theoretical production rate of micrograms per run, modification of the microcarrier substrate (e.g., to increase porosity) and/or of the LSBAW architecture (to improve acoustic field focusing through pillar design or to enhance trapping capacity through traditional acoustic separation device scaling) can allow for greater yield.

When introducing elements of the present disclosure or embodiments thereof, the articles "a," "an," "the," and "said" are intended to mean that there are one or more of the elements. The terms "comprising," including," and "having" are intended to be inclusive and mean that there may be additional elements other than the listed elements.

In view of the above, it will be seen that the several advantages of the disclosure are achieved and other advantageous results attained. As various changes could be made in the above processes and composites without departing from the scope of the disclosure, it is intended that all matter contained in the above description and shown in the accompanying drawings shall be interpreted as illustrative and not in a limiting sense.

What is claimed is:

1. A method for isolating mammalian cells under continuous flow conditions, the method comprising:
   providing a plurality of mammalian cells;
   loading the plurality of mammalian cells into an acoustic separation device, wherein the acoustic separation device comprises:
   an inlet;
   an outlet;
   a channel coupled to the inlet and the outlet, wherein the channel defines a flow path between the inlet and the outlet;
   a standing acoustic wave generating device; and
   at least one pillar array comprising a plurality of pillars, wherein the at least one pillar array is situated within the flow path defined by the channel, wherein the at least one pillar array comprises a first pillar array and a second pillar array, wherein the first pillar array is substantially parallel to the second pillar array, wherein the first pillar array and the second pillar array form an enrichment structure;
   generating an augmented pressure field comprising locally augmenting, by the enrichment structure, a pressure field generated by the standing acoustic wave generating device; and
   isolating at least one of the plurality of mammalian cells by using the augmented pressure field to facilitate retention of the at least one of the plurality of mammalian cells at a single lateral location within the flow path.

2. The method of claim 1, wherein the plurality of pillars comprises individual pillars, wherein the individual pillars comprise a first side with a first thickness and a second side with a second thickness, wherein the first thickness is greater than the second thickness.

3. The method claim 2, wherein the plurality of pillars is oriented such that the first sides of the pillars are substantially perpendicular to the flow path.

4. The method of claim 2, wherein the plurality of pillars is oriented such that the first sides of the pillars are at an angle of between about 60-90° relative to the flow path.

5. The method of claim 2, wherein the ratio of the second thickness to the first thickness is between about 0.01-0.9.

6. The method of claim 1, wherein an average distance between the first pillar array and a second pillar array is between about 0.1 mm and 2.5 mm.

7. The method of claim 1, wherein the channel is separated from the standing acoustic wave generating device.

8. The method of claim 1, wherein the plurality of pillar pairs occupy a common plane, and wherein the common plane is parallel to the channel.

9. The method of claim 1, wherein the plurality of pillar pairs occupy a common plane, and wherein the common plane is perpendicular to the channel.

10. A method for enriching mammalian cells under continuous flow conditions, the method comprising:
    providing a plurality of mammalian cells;
    loading the plurality of mammalian cells into an acoustic separation device, wherein the acoustic separation device comprises:
    an inlet;
    an outlet;
    a channel coupled to the inlet and the outlet, wherein the channel defines a flow path between the inlet and the outlet;
    a standing acoustic wave generating device; and at least one pillar array comprising a plurality of pillars, wherein the at least one pillar array is situated within the flow path defined by the channel, wherein the at least one pillar array comprises a first pillar array and a second pillar array, wherein the first pillar array is substantially parallel to the second pillar array, wherein the first pillar array and the second pillar array form an enrichment structure;

generating an augmented pressure field comprising locally augmenting, by the enrichment structure, a pressure field generated by the standing acoustic wave generating device; and retaining, using the augmented pressure field, at least one of the plurality of mammalian cells at a single lateral location within the flow path; and sequentially performing a plurality of reagent introduction and washing steps to the at least one retained mammalian cell to produce a final enriched mammalian cell product.

11. The method of claim 10, wherein the acoustic separation device further comprises a plurality of wells configured to hold a plurality of substances required for a reagent manipulation sequence.

12. The method of claim 11, wherein the acoustic separation device further comprises a pump configured to distribute the plurality of substances according to the reagent manipulation sequence.

13. The method of claim 10, wherein the plurality of pillars comprises individual pillars, wherein the individual pillars comprise a first side with a first thickness and a second side with a second thickness, wherein the first thickness is greater than the second thickness.

14. The method claim 13, wherein the plurality of pillars is oriented such that the first sides of the pillars are substantially perpendicular to the flow path.

15. The method claim 13, wherein the plurality of pillars is oriented such that the first sides of the pillars are at an angle of between about 60-90° relative to the flow path.

16. The method of claim 13, wherein the ratio of the second thickness to the first thickness is between about 0.01-0.9.

17. The method of claim 10, wherein an average distance between the first pillar array and a second pillar array is between about 0.1 mm and 2.5 mm.

18. The method of claim 10, wherein the channel is separated from the standing acoustic wave generating device.

19. The method of claim 10, wherein the plurality of pillar pairs occupy a common plane, wherein the common plane is parallel or perpendicular to the channel.

20. A method for enriching microorganisms under continuous flow conditions, the method comprising:

providing a plurality of microorganisms;

loading the plurality of microorganisms into an acoustic separation device, wherein the acoustic separation device comprises:
an inlet;
an outlet;
a channel coupled to the inlet and the outlet, wherein the channel defines a flow path between the inlet and the outlet;
a standing acoustic wave generating device; and
at least one pillar array comprising a plurality of pillars, wherein the at least one pillar array is situated within the flow path defined by the channel, wherein the at least one pillar array comprises a first pillar array and a second pillar array, wherein the first pillar array is substantially parallel to the second pillar array, wherein the first pillar array and the second pillar array form an enrichment structure;

generating an augmented pressure field comprising locally augmenting, by the enrichment structure, a pressure field generated by the standing acoustic wave generating device; and retaining, using the augmented pressure field, at least one of the plurality of microorganisms at a single lateral location within the flow path; and sequentially performing a plurality of reagent introduction and washing steps to the at least one retained microorganism to produce a final enriched microorganism product.

* * * * *